United States Patent
Ferber et al.

(10) Patent No.: US 12,303,293 B2
(45) Date of Patent: *May 20, 2025

(54) SYSTEMS AND METHODS FOR COMPUTATIONALLY EFFICIENT NON-INVASIVE BLOOD QUALITY MEASUREMENT

(71) Applicant: Itamar Medical Spry 2021, Limited Partnership, Chelmsford, MA (US)

(72) Inventors: Elad Ferber, Mountain View, CA (US); Andrew Joseph DeKelaita, Belmont, CA (US); Patrick Edward Landreman, Palo Alto, CA (US)

(73) Assignee: Itamar Medical Spry 2021, Limited Partnership, Caesarea (IL)

( * ) Notice: Subject to any disclaimer, the term of this patent is extended or adjusted under 35 U.S.C. 154(b) by 293 days.

This patent is subject to a terminal disclaimer.

(21) Appl. No.: 17/809,100

(22) Filed: Jun. 27, 2022

(65) Prior Publication Data
US 2023/0148961 A1 May 18, 2023

Related U.S. Application Data

(63) Continuation of application No. 17/699,596, filed on Mar. 21, 2022, now abandoned, which is a
(Continued)

(51) Int. Cl.
*A61B 5/00* (2006.01)
*A61B 5/024* (2006.01)
*A61B 5/08* (2006.01)

(52) U.S. Cl.
CPC ............ *A61B 5/681* (2013.01); *A61B 5/0004* (2013.01); *A61B 5/02427* (2013.01); *A61B 5/08* (2013.01);
(Continued)

(58) Field of Classification Search
USPC ................................................. 600/300–301
See application file for complete search history.

(56) References Cited

U.S. PATENT DOCUMENTS 8,437,824 B2  5/2013  Moon et al.
9,220,440 B2  12/2015  Addison et al.
(Continued)

OTHER PUBLICATIONS

International Search Report and Written Opinion of International Searching Authority for PCT/US2020/015500, ISA/US, Alexandria, VA, Dated: Mar. 25, 2020.
(Continued)

*Primary Examiner* — Joseph M Dietrich
*Assistant Examiner* — Michael T. Holtzclaw
(74) *Attorney, Agent, or Firm* — The Webb Law Firm

(57) ABSTRACT

A system includes a wearable member configured to receive first energy, generate first signals, select a first subset of the time series data, determine a standard deviation indicating a quality at a low percentile of values associated with first windows of the time series data and a high percentile of values associated with the first windows of the time series data, the signal assessment threshold being including at least the values of the lower percentile, receive second energy, generate second signals containing second time series data from the second energy, select a second subset of the time series data to assess, compare all or part of the second signals to the signal assessment threshold, and if all or part of the second signals include the second time series data that is within the values of the lower percentile, then remove the second signals from further processing.

23 Claims, 14 Drawing Sheets

Related U.S. Application Data continuation of application No. 16/775,256, filed on Jan. 28, 2020, now Pat. No. 11,311,237.

(60) Provisional application No. 62/797,909, filed on Jan. 28, 2019, provisional application No. 62/797,912, filed on Jan. 28, 2019.

(52) U.S. Cl.
CPC .......... *A61B 5/7203* (2013.01); *A61B 5/7221* (2013.01); *A61B 5/7264* (2013.01); *A61B 5/7275* (2013.01)

(56) References Cited

U.S. PATENT DOCUMENTS

| | | |
|---|---|---|
| 2010/0331724 A1 | 12/2010 | Watson et al. |
| 2016/0287110 A1 | 10/2016 | Morris et al. |
| 2016/0302706 A1 | 10/2016 | Richards et al. |
| 2017/0119315 A1 | 5/2017 | LeBoeuf et al. |
| 2017/0311902 A1 | 11/2017 | Ferber et al. |
| 2018/0085040 A1 | 3/2018 | Ferber et al. |

OTHER PUBLICATIONS

Wyser et al. Wearable and modular near-infrared spectroscopy instrument with multidistance measurements at four wavelengths. Aug. 18, 2017 (Aug. 18, 2017). [retrieved on Mar. 25, 2020[. Retrieved from the Internet: URL: https://www.ncbi.nlm.nih.gov/pmc/atricles/PMC5562388/ entire document.

Yan et al., A multi-Wavelength Opto-Electronic Patch Sensor to Effectively Detect Physiological . . . , Changes against Human Skin Types. Jun. 21, 2017 (Jun. 21, 2017). [retrieved on Mar. 25, 2020]. Retrieved from the Internet: URL: https://www.ncbi.nih.gov/pubmed/28635643 pp. 1-12.

SYSTEMS AND METHODS FOR COMPUTATIONALLY EFFICIENT NON-INVASIVE BLOOD QUALITY MEASUREMENT

CROSS-REFERENCE TO RELATED APPLICATIONS

The present application is a continuation of U.S. patent application Ser. No. 17/699,596 filed Mar. 21, 2022, which is a continuation of U.S. patent application Ser. No. 16/775,256 filed Jan. 28, 2020, which issued as U.S. Pat. No. 11,311,237 on Apr. 26, 2022, which claims the benefit of U.S. Provisional Patent Application No. 62/797,909 filed Jan. 28, 2019 and U.S. Provisional Patent Application No. 62/797,912 filed Jan. 28, 2019, the entire contents of which are incorporated by reference herein.

BACKGROUND

Technical Field

Embodiments of the present inventions relate generally to blood metrics measurement. More specifically, embodiments of the present inventions relate to non-invasive respiratory rate measurement.

Description of Related Art

Wearable activity monitoring devices are growing in popularity. These devices aim to facilitate achieving a user's goal such as to lose weight, to increase physical activity, or simply to improve overall health. Many such devices may interface with computer software to allow visualization of the recorded data. Nevertheless, most devices are evolved cousins of pedometers, which measure the number of steps a user takes. Even though additional functions such as tallying the distance a user travels or calculating calorie consumptions may be added, these devices lack the ability to measure blood metrics.

Respiratory rate may be measured along with other vital signs, such as heart rate, blood pressure and body temperature. Respiratory rate may be an indicator of the performance of the various systems of the body, and may be a predictor of adverse events, such as cardiac arrest or sleep apnea. However, the level of recordation of vital signs, especially respiration rate, in many environments (e.g., hospitals) may be poor or even non-existent.

SUMMARY

An example method comprises receives, from a wearable sensor device, first energy from at least one LED of the wearable sensor device, the first energy being at a wavelength to take a physiological measurement, generating, by the wearable sensor device, first signals containing first time series data from the first energy, selecting, by the wearable sensor device, a first subset of the time series data to generate a signal assessment threshold, determining a standard deviation indicating a quality at a low percentile of values associated with first windows of the time series data and a high percentile of values associated with the first windows of the time series data, the signal assessment threshold being including at least the values of the lower percentile, receiving, from the wearable sensor device, second energy from at least one LED of the wearable sensor device, the second energy being at the wavelength to take the physiological measurement of a wearer of the wearable sensor device, generating, by the wearable sensor device, second signals containing second time series data from the second energy, selecting a second subset of the time series data to assess prior to processing the time series data of the second subset and other time series data taken near or at a same time as the generation of the second signals, comparing all or part of the second signals to the signal assessment threshold, and if all or part of the second signals include the second time series data that is within the values of the lower percentile based on the signal assessment threshold, then removing the second signals from further processing.

In various embodiments, if all or part of the second signals include second time series data that is within the values of the upper percentile based on the signal assessment threshold, then the method may comprise removing the second signals from further processing. In some embodiments, if all or part of the second signals include second time series data that is not within the values of the upper percentile and not within the values of the lower percentile based on the signal assessment threshold, then the method may comprise processing the second signals to take the physiological measurement. In some embodiments, the physiological measurement is a respiratory rate. In various embodiments, the physiological measurement is a SpO2 measurement.

The first energy may be at the wavelength to take the physiological measurement of the wearer of the wearable sensor device. In some embodiments, the method comprises wherein if all or part of the second signals include the second time series data that is above the values of the lower percentile based on the signal assessment threshold, then processing the second signals to make measurements.

If all or part of the second signals include the second time series data that is above the values of the lower percentile based on the signal assessment threshold, then the method may comprise the third signals to make measurements, the third signals being generated by a location associated with low SNR.

Determining the standard deviation indicating a quality at a low percentile of values associated with first windows of the time series data and a high percentile of values associated with the first windows of the time series data may comprise computing a normalized standard deviation of the window:

$$\sigma_s = \frac{\sqrt{\frac{1}{N}\sum_i (x_i - x)^2}}{x}$$

Where:

$$x = \frac{1}{N}\sum_i x_i$$

An example system comprises a wearable member including a processor and memory to store executable instructions, the instructions being executable to: receive first energy from at least one LED of the wearable sensor device, the first energy being at a wavelength to take a physiological measurement, generate first signals containing first time series data from the first energy, select a first subset of the time series data to generate a signal assessment threshold, determine a standard deviation indicating a quality at a low percentile of values associated with first windows of the time series data and a high percentile of values associated with the first windows of the time series data, the signal assessment threshold being including at least the values of the lower percentile, receive second energy from at least one LED of the wearable sensor device, the second energy being at the wavelength to take the physiological measurement of a wearer of the wearable sensor device, generate second signals containing second time series data from the second energy, select a second subset of the time series data to assess prior to processing the time series data of the second subset and other time series data taken near or at a same time as the generation of the second signals, compare all or part of the second signals to the signal assessment threshold, and if all or part of the second signals include the second time series data that is within the values of the lower percentile based on the signal assessment threshold, then remove the second signals from further processing.

Another example system may include a processor and memory storing instructions that, when executed by the processor, cause the processor to receive first energy from at least one LED of the wearable sensor device, the first energy being at a wavelength to take a physiological measurement, generate first signals containing first time series data from the first energy, select a first subset of the time series data to generate a signal assessment threshold, determine a standard deviation indicating a quality at a low percentile of values associated with first windows of the time series data and a high percentile of values associated with the first windows of the time series data, the signal assessment threshold being including at least the values of the lower percentile, receive second energy from at least one LED of the wearable sensor device, the second energy being at the wavelength to take the physiological measurement of a wearer of the wearable sensor device, generate second signals containing second time series data from the second energy, select a second subset of the time series data to assess prior to processing the time series data of the second subset and other time series data taken near or at a same time as the generation of the second signals, compare all or part of the second signals to the signal assessment threshold, and if all or part of the second signals include the second time series data that is within the values of the lower percentile based on the signal assessment threshold, then remove the second signals from further processing.

DETAILED DESCRIPTION

Biometrics including blood metrics may be measured by minimally invasive procedures to address medical conditions such as diabetes or in the diagnosis and discovery of diseases. Minimal-invasive procedure based devices may have the advantages of reducing costs and decreasing the need for invasive methods, thereby increasing the comfort and well-being of users and patients. Even though these devices have revolutionized patient care, they have only been described in, and approved for, medical purposes. Minimal-invasive procedure based devices are usually out of reach for the general public because they are designed for medical uses rather than non-medical purposes such as fitness, well-being, and quality of life.

Personal devices such as sphygmomanometers or pulse oximeters measure blood pressure or oxygen levels, respectively, on a per-request basis. They usually cannot measure blood metrics real time or periodically. Real-time blood metrics data (e.g., high resolution measurements, or measurements over long periods of time) may allow these devices to facilitate users monitoring and controlling their energy levels and/or metabolism. Nutritionists, people suffering from obesity, people desiring to eat healthier, fitness enthusiasts, semi-professional athletes, people likely to have hypoglycemia, or the vast majority of the general population can benefit from these devices.

In various embodiments, a multispectral blood metric measurement apparatus monitors blood metrics, fitness, and/or metabolism levels of various users in a non-invasive manner. The multispectral blood metric measurement apparatus may be, for example, wearable technology. The multispectral blood metric measurement apparatus may measure any number of blood metrics. Blood metrics may include, for example, various nutrient blood concentrations. Blood metrics may be, for example, monitored, stored, tracked, and/or analyzed.

Figure 1:
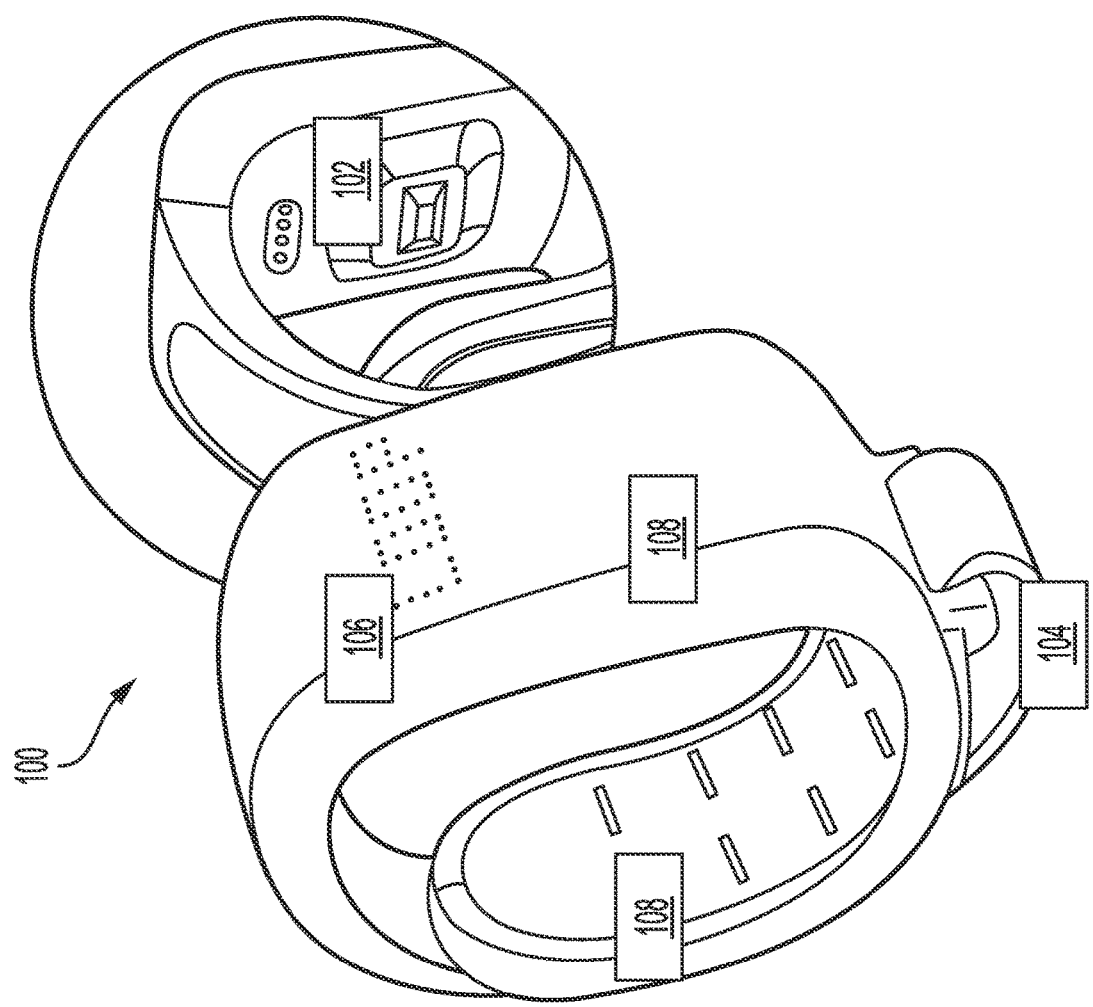
FIG. 1 depicts an example wearable sensor device in some embodiments.

FIG. 1 depicts an example wearable sensor device 100 in some embodiments. The wearable sensor device 100 may perform passive, non-invasive, intermittent data collection of physiological parameters of a wearer. The physiological parameters may be assessed by the wearable sensor device 100 and/or provided to a remote device such as a server accessible by a clinician. The wearable sensor device 100 may measure and record, for example, arterial oxygen saturation (SpO2), heart rate (HR), respiration rate (RR), and/or blood pressure (BP). The wearable sensor device 100 may or may not provide physiological alarms to the wearer.

In various embodiments, the wearable sensor device 100 may determine heart rate and/or blood pressure from PPG signals.

The wearable sensor device 100 may noninvasively measure and/or estimate a patient's physiological parameters derived from light reflected off the wearer's wrist. In one example, the wearable sensor device 100 shines light into the wrist tissue of the wearer and analyzes the differences in intensity of the reflected light. The light absorbance in the tissue changes depending on the concentration of oxygenated hemoglobin in the blood. A set of formulas based on the Beer-Lambert law is used to derive the measured SpO2 (peripheral oxygen saturation) from that reflected light.

The wearable sensor device 100 depicted in FIG. 1 may include a band connector 102, a strap 104, an LED screen 106, an LED array 108 including a plurality of LEDs. It may be appreciated that the band of the wearable sensor device 100 holds the LED screen 106, the LED array 108, and the plurality of LEDs. The band may hold the LED array 108 and the plurality of LEDs at predetermined distances from each other, thereby enable sensors to receive different light and make different measurements.

The band connector 102 may connect the band to an internal device with a processor and memory. The processor and memory may control the operation of the wearable sensor device 100 and provide data to remote devices (e.g., via wired or wireless connectivity).

The strap 104 may enable the wearable sensor device 100 to be adjusted for different wrist sizes and enable the wearable sensor device 100 to be put on and taken off by a wearer.

The LED screen 106 may depict information to the wearer, including measurements and/or estimates for arterial oxygen saturation (SpO2), heart rate (HR), respiration rate (RR), and/or blood pressure (BP). The LED screen 106 may also indicate any errors, battery state, and the like. In various embodiments, the wearable sensor device 100 may include a touch sensor (e.g., within the internal device) that enables a wearer to touch a part of the band (e.g., the LED screen 106 and/or the face of the band that includes the LED screen 106) to change the LED screen 106 and/or command functionality.

The LED array 108 may be positioned on an inner member of the band. In various embodiments, the inner member of the band is pushed by the strap 104 against the wrist of the wearer. In one example, by adjusting the strap, a plurality of LED arrays may be pushed against the bottom of the wrist below the palm of the wearer's hand. In some embodiments, one or more of the LED arrays may be pushed against a side or edge of the wearer's wrist. The LED array 108 may include any number of sensors configured to receive light from one or more of the plurality of LEDs. The LED array 108 may include any number of sensors configured to receive one or more different wavelengths of light.

The plurality of LEDs may be on one side of the band opposite the LED screen. The plurality of LEDs may be facing the wearer's wrist (e.g., the top of the wearer's wrist closest to the back of the wearer's hand). The plurality of LEDs may include any number of LEDs at many different wavelengths. In one example, the plurality of LEDs include green, red, and infrared. It may be appreciated that there may be any number of wavelengths of light emitted by any number of LEDs of the plurality of LEDs.

The following are example LED performance of the plurality of LEDs in one embodiment:
LED #1—Red
    Peak emission wavelength: 660 nm
    Mean radiant intensity: 142 uW/sr
    Mean radiant intensity in the axial direction: 71.1 uW/sr
LED #2—Green
    Peak emission wavelength: 526 nm
    Mean radiant intensity: 106 uW/sr
    Mean radiant intensity in the axial direction: 36 uW/sr
LED #3—Infrared
    Peak emission wavelength: 950 nm
    Mean radiant intensity: 106 uW/sr
    Mean radiant intensity in the axial direction: 53 uW/sr There may be a power port may be configured to be able to be coupled to a power cable for powering the wearable sensor device 100. In various embodiments, the internal device includes a power storage device as well as the processor and memory. The internal device may be coupled to the power port and configured to receive and/or store power.

Figure 2:
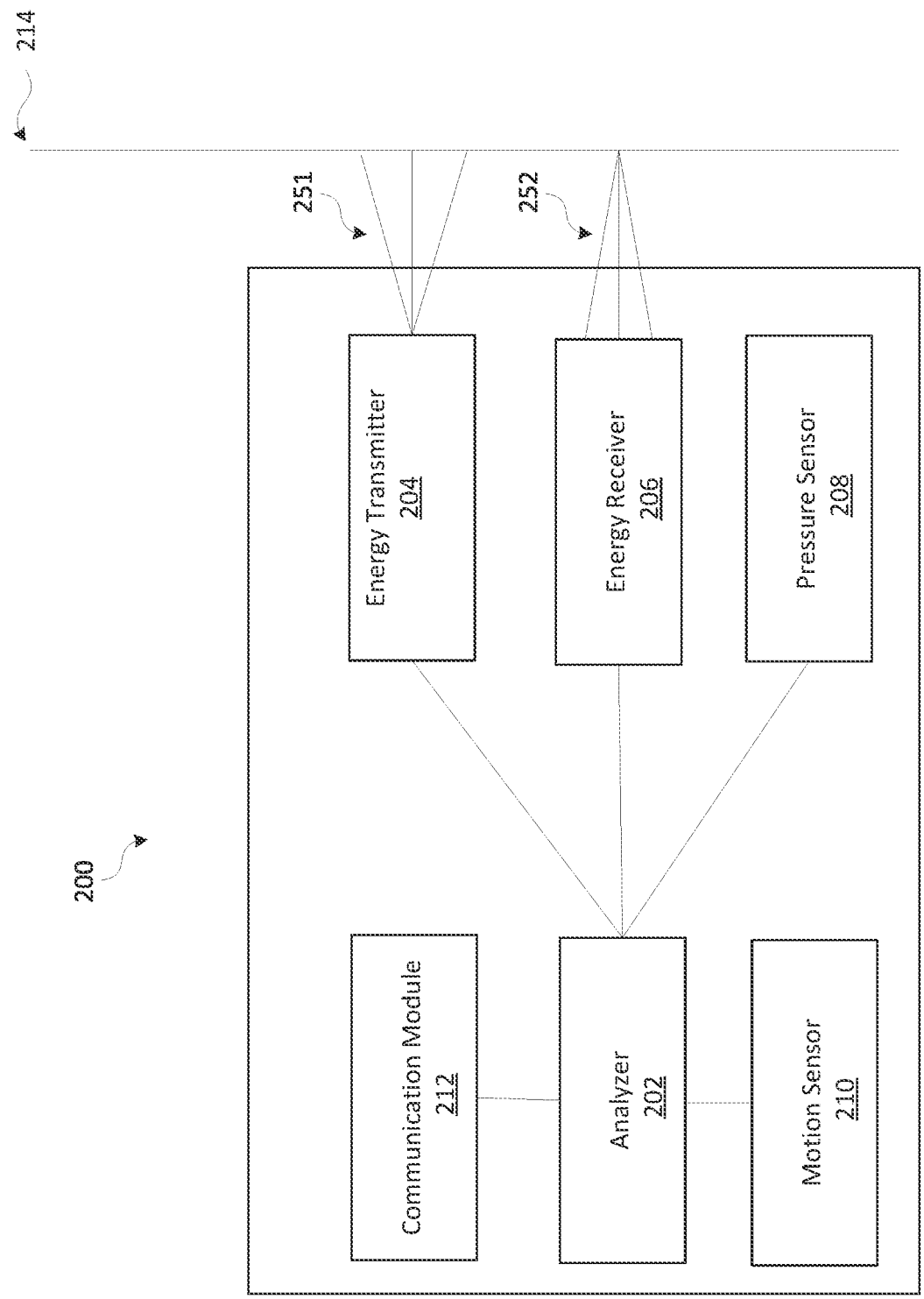
FIG. 2 depicts a block diagram of a blood metrics measurement apparatus according to some embodiments.

In one example of an embodiment, the wearable sensor device 100 may perform SpO2 and heart rate measurements with the following performance:
SpO2
    Display Range: 0% to 100%
    Measurement Range: 70% to 100%
    Accuracy: 3.5%
Heart Rate
    Display Range: 15-250 bpm
    Measurement Range: 15-250 bpm
    Accuracy: +/−3 bpm FIG. 2 depicts a block diagram 200 of a blood metrics measurement apparatus 200 according to some embodiments. The blood metrics measurement apparatus 200 may be a wearable sensor device such as the wearable sensor device 100. The blood metrics measurement apparatus 200 may be, for example, a wearable apparatus including any number of energy transmitters 204 and energy receivers 206.

The blood metrics measurement apparatus 200 comprises an analyzer 202, an energy transmitter 204, an energy receiver 206, a pressure sensor 208, a motion sensor 210, and a communication module 212. The blood metrics measurement apparatus 200 may be, include, or be a part of a wearable member. The wearable member may include, for example, a bracelet, glasses, necklace, ring, anklet, belt, broach, jewelry, clothing, or any other member of combination of members that allow the blood metrics measurement apparatus 200 to be close to or touch a body of the wearer. In some embodiments, the blood metrics measurement apparatus 200 may further comprise a driver (not shown) and a power source (not shown). The power source may be coupled to the energy transmitter 204 via the driver. The blood metrics measurement apparatus 200 may also comprise an Analog-to-Digital Converter ("ADC") (not shown). In one example, the ADC may be coupled to the energy receiver 206 and the analyzer 202.

The analyzer 202 may be coupled to the energy transmitter 204, the energy receiver 206, the pressure sensor 208, the motion sensor 210, and the communication module 212. The energy transmitter 204 and the energy receiver 206 may be secured to the wearable member such that the energy transmitter 204 and the energy receiver 206 may make contact or be in proximity with tissues (e.g., skin) of a user.

In various embodiments, the energy transmitter 204 emits energy including, but not limited to, light, into the body of the user. The energy produced by the energy transmitter may be in the direction of entering tissues. For example, the energy produced by the energy transmitter 204 is in a direction 251 entering the tissue 214. In some embodiments, the energy transmitter 204 emits energy or light at different wavelengths. The energy transmitter 204 may comprise any number of light emitting diodes ("LEDs"). In some embodiments, the energy transmitter 204 comprises at least two LEDs. Each LED may be configured to emit energy at one or more wavelengths. In another example, each LED may emit light with a peak wavelength centered around a wavelength. In one example, the energy transmitter 204 may emit light with a peak wavelength centered around 500 nm to 1800 nm, although the wavelength may include a variety of spectrums (e.g., IR, near-IR, and the like).

Each wavelength may correspond to one or more blood metrics of interest and/or one or more nutrients. It will be appreciated that different components of the blood and/or different nutrients may absorb energy at different wavelengths. In various embodiments, a controller, driver, analyzer 202, or the like may receive a blood metric or nutrient of interest (e.g., from a user of the blood metrics measurement apparatus 200 and/or a user device not shown). The controller, driver, analyzer 202 or the like may associate the blood metric and/or nutrient of interest with one or more wavelengths and configure one or more of the LEDs to emit energy of at least one of the one or more wavelengths. For example, the analyzer 202 may command the driver to deliver electric power to one LED that is configured to emit light at the desired wavelength.

The energy receiver 206 may detect energy associated with the energy provided by the LEDs from tissues (e.g., skin) of the user. In this example, received and/or detected energy is in the direction 252 that leaves from the tissue 214. In various embodiments, the energy receiver 206 may detect energy from the body of the user that is a fraction of the energy produced by the energy transmitter 204.

The energy transmitter 204 and the energy receiver 206 may be configured such that the energy receiver 206 detects reflected energy from tissues of the user of the multispectral blood metrics measurement apparatus 200. For example, the energy transmitter 204 and the energy receiver 206 may be configured to be disposed on one surface or side of a user's tissue. The energy transmitter 204 and the energy receiver 206 may be configured such that the energy receiver 206 detects energy from the energy transmitter 204 that passes through or reflects from the user's tissues. In some embodiments, the energy transmitter 204 and the energy receiver 206 may be configured to be disposed on different (e.g., opposite) surfaces or sides of a users' tissue.

The energy transmitter 204 may be configured to generate energy at a set of wavelengths. In some embodiments, the energy transmitter 204 generates energy at different wavelengths sequentially and/or periodically. For example, the energy transmitter 204 may be configured to generate energy at each particular wavelength until energy at all wavelengths of the set is generated. The period of time for the energy transmitter 204 to generate energy at all wavelengths of the set is a generation period. Subsequent to completion of the generation period, the energy transmitter 204 may start a new generation period thereby allowing multiple measurements.

Energy detected from tissues of a user may be detected by the energy receiver 206. The energy receiver 206 may be configured to generate a signal in response to the detected energy. In some embodiments, the energy receiver 206 may be triggered by the energy received to generate an output which may be dependent or partially dependent upon the amount of energy received. The energy receiver 206 may be configured to generate a signal (e.g., an electric current, or an electric voltage) in response to the energy received from the tissues.

The signal generated by the energy receiver 206 may be associated with one or more blood metrics and/or nutrients of interest. Energy at different wavelengths may be absorbed at a different rate that is related to a user's body state. The user's body state (e.g., heart rate, blood pressure, nutrient level, or the like) may determine the amount of energy absorbed by the body. Accordingly, energy from the user's body at different wavelengths may be detected at different levels thereby causing different responses of the energy receiver 206. The energy receiver 206 may, for example, output signals based on the level of the energy received.

The energy receiver 206 may provide information associated with the user's body state. Blood metric information may be determined (e.g., by the analyzer 202) from the output signal of the energy receiver 206. In some embodiments, the energy receiver 206 may comprise a set of photodetectors (e.g., a photodiode, or a phototransistor) which are configured to output a signal dependent upon photons or the like from the energy transmitter 204 that passed through tissues of the user.

In various embodiments, the output signal of the energy receiver 206 is a composite of multiple signals. Each signal of the composite may be associated with energy at a wavelength which may be a portion (or fraction) of the total energy emitted by the energy transmitter 204.

The pressure sensor 208 may be configured to generate, detect, and/or measure non-optical signals. For example, the pressure sensor 208 may non-invasively and continuously generate, detect, and/or measure pressure pulse signals.

In some embodiments, the motion sensor 210 may be configured to detect position and orientation of the blood metrics measurement apparatus 200, and detect motion of the blood metrics measurement apparatus 200. For example, the blood metrics measurement apparatus 200 may detect position, orientation, and motion along an x, y, or z-axis, and measured values may include velocity, acceleration, distance, and the like. In some embodiments, the motion sensor 210 may include one or more accelerometers, gyroscope, global positioning systems, or the like. The motion sensor may be coupled to the analyzer 202.

The communication module 212 may be configured to send requests to and receive data from one or a plurality of systems. The communication module 212 may send requests to and receive data from systems through a network or a portion of a network. Depending upon implementation-specific or other considerations, the communication module 212 may send requests and receive data through a connection (e.g., the communication link 910), all or a portion of which may be a wireless connection. The communication module 212 may request and receive messages, and/or other communications from associated systems.

Figure 3:
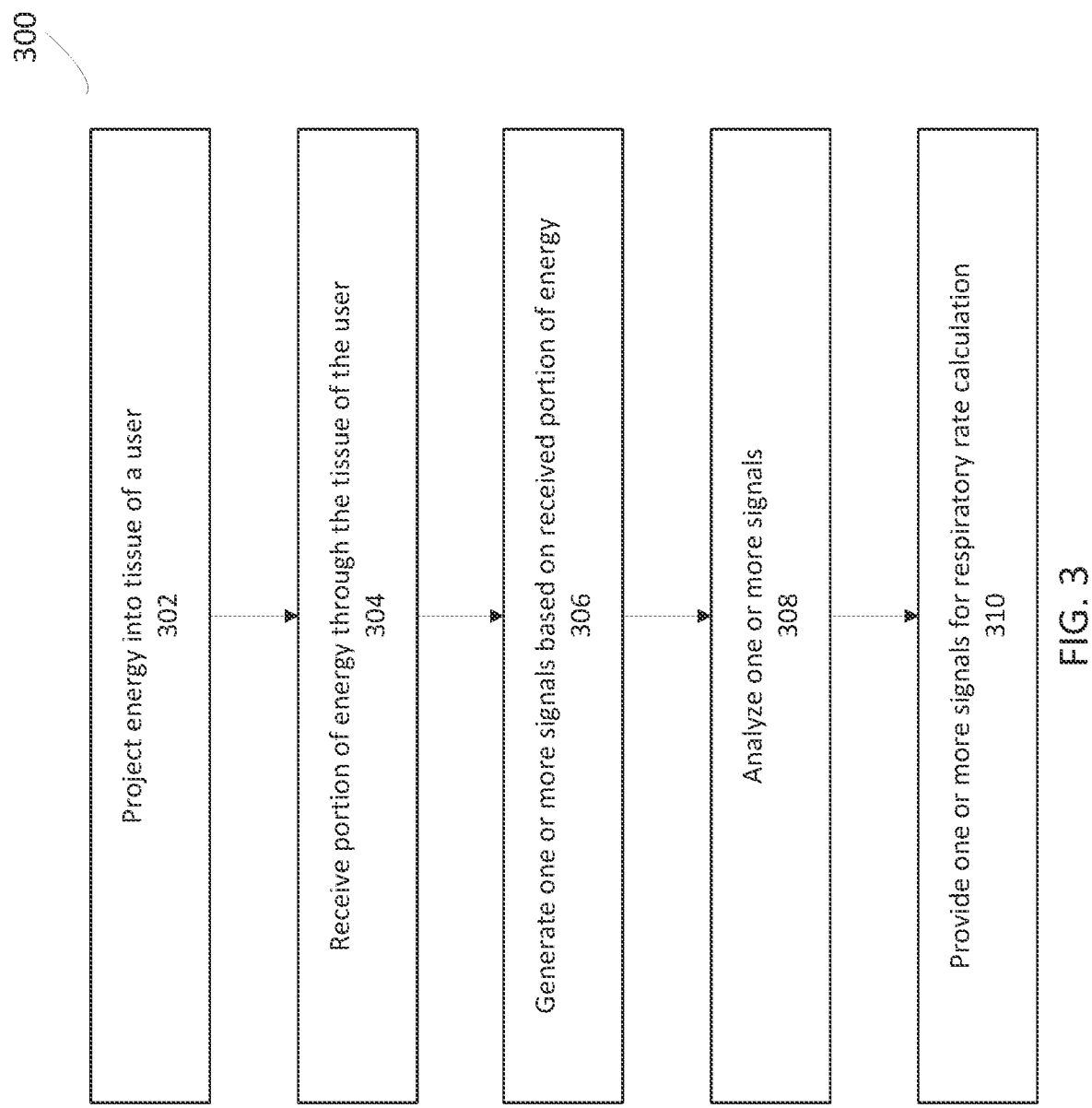
FIG. 3 depicts a flowchart of an example method of operation of a blood metrics measurement apparatus (e.g., blood metrics measurement apparatus) according to some embodiments.

FIG. 3 depicts a flowchart 300 of an example method of operation of a blood metrics measurement apparatus (e.g., blood metrics measurement apparatus 200) according to some embodiments. In this and other flowcharts described herein, the flowchart illustrates by way of example a sequence of steps. It should be understood the steps may be reorganized for parallel execution, or reordered, as applicable. Moreover, some steps that could have been included may have been removed to avoid providing too much information for the sake of clarity and some steps that were included could be removed, but may have been included for the sake of illustrative clarity.

In step 302, a blood metrics measurement apparatus projects energy into tissue of a user (e.g., the user wearing blood metrics measurement apparatus). The energy may be projected from an energy transmitter (e.g., energy transmitter 204, FIG. 2) comprising a plurality of light sources (e.g., LEDs). In some embodiments, a first light source (e.g., one or more LEDs) may project light energy at a plurality of different wavelengths, such as 523 nm, 590 nm, 623 nm, 660 nm, 740 nm, 850 nm, and 940 nm, and a second light source (e.g., one or more LEDs) may project energy at the same, or substantially similar, wavelength as one of the wavelengths projected by the first light source (e.g., 523 nm, 590 nm, 623 nm, 660 nm, 740 nm, 850 nm, or 940 nm). It will be appreciated that other configuration may be used (e.g., a greater number of light sources) a greater or lesser number of wavelengths projected from the lights sources, and so forth.

In step 304, the blood metrics measurement apparatus receives (or, "detects) portions of energy through the tissue of the user. In some embodiments, an energy receiver (e.g., energy receiver 1006) detects a portion of the energy transmitted into the user's tissue by the energy transmitter. The energy receiver may generate a signal based on the portion of energy detected (e.g., based on the amount of the energy detected). For example, energy detected may be a portion of the energy projected at step 302 reflected by the tissue. By way of further example, energy detected may be a portion of the energy projected at step 302 that passes through the tissue (e.g., other undetected energy may be absorbed by tissue and/or otherwise blocked). In various embodiments, steps 302 and 304 are performed simultaneously or substantially simultaneously. That is, energy projection and detection may be performed approximately simultaneously.

In step 306, the blood metrics measurement apparatus generates one or more signals based on the received portions of energy. In some embodiments, the energy receiver may generate a multichannel PPG signal (e.g., as mentioned above). The output (or, "generated") signal of the energy receiver may be an electric current or an electric voltage, of which the amplitude may be related to the amount of the energy detected.

In various embodiments, analysis of the signals from the energy receiver may identify abnormal measurements. For example, each of the measurements may be compared to a predetermined value. If the difference between the measurement and the predetermined value is above (or below) a threshold, then the measurement may be determined to be abnormal. An abnormal value may trigger additional analysis or an alert. In some embodiments, an abnormal value is ignored (e.g., as possibly affected by noise caused by movement of the energy transmitter and/or the energy receiver). In various embodiments, the abnormal value may be discounted (e.g., the weight of the value reduced). The degree of discount may be based, for example, on information from an accelerometer (e.g., a large acceleration may indicate that the abnormal value should be significantly discounted) and/or based on historical values. It will be appreciated that the degree of discount may be based on any number of factors.

In some embodiments, measurements may be averaged over a period of time. A Kalman filter (e.g., a nonlinear, unscented Kalman filter) may be applied to any number of measurements or averaged measurements. A motion measurement (e.g., a measurement by an accelerometer) may be considered. Upon determining a measurement is abnormal, the motion measurement for that time point may be inspected. A large measurement may indicate large vibrations or accelerations that corroborate that the measurement may be abnormal. Measurements collected in such situations are likely to have significant electrical noises.

At step 308, the blood metrics measurement apparatus (e.g., blood metrics measurement apparatus 200) analyzes signals from the energy receiver analyzed in the frequency domain to determine blood metrics. Concentration of a nutrient in the blood may subsequently be determined. In some embodiments, signals may be provided to a bandpass filter that separates AC components from DC components. An AC component may represent signal variation at the cardiac frequency and a DC component may represent the average overall transmitted light intensity. In some embodiments, a heart rate and/or oxygen saturation, SpO2 may be determined. The heart rate may be determined, for example, by averaging the maximum frequency to determine the rate of cardiac beats in a predetermined amount of time. The oxygen saturation SpO2 may be determined according to Equation (1):

$$S_pO_2 = 110 - 25 \times R \qquad (1),$$

where R is the ration of a red and infrared normalized transmitted light intensity. R may be determined according to Equation (2):

$$R = \frac{AC_R/DC_R}{AC_{IR}/DC_{IR}}, \qquad (2),$$

where the $AC_R$ is the AC component of the detected energy corresponding to a wavelength (e.g., red light), $DC_R$ is the DC component of the detected energy corresponding to the wavelength (e.g., red light), $AC_{IR}$ is the AC component of the detected energy corresponding to a different wavelength (e.g., infrared light), and $DC_{IR}$ is the DC component of the detected energy corresponding to the different wavelength (e.g., infrared light). In some embodiments, the AC component may be selected as the highest spectral line in the cardiac frequency band. Waveform analysis may be performed to determine the R-R interval defined by two successive AC components, an elapsed interval and the probation, if there is any.

It will be appreciated that analysis may be performed by the analyzer and/or any other digital device (e.g., user device or a blood metrics server such as a blood metrics server).

State space estimation and progression may be performed to determine blood metrics. A system may be modeled according to Equation (3):

$$x(n+1) = f[x(n)] + u(n)$$

$$y(n) = h[x(n)] + v(n) \qquad (3),$$

where x(n) represents the state of the system, u(n) is process noise, y(n) is the vector of the observed signals, and v(n) is the measurement noise.

Table 1 lists one or more parameters for x(n) as well as their initial value in some embodiments:

TABLE 1

| Parameter | Symbol | Initial Value |
|---|---|---|
| Cardiac frequency | $f_{HR}$ | 1 Hz |
| Cardiac phase | $\theta_{HR}$ | 0 |

TABLE 1-continued

| Parameter | Symbol | Initial Value |
|---|---|---|
| Cardiac harmonic amplitude | $I_{HARMONIC}^{HR}$ | 0 |
| Cardiac Pulse Pressure | $P_{HR}$ | 1 |
| Point Blood Pressure | $P_{Point}$ | 1 |
| Respiratory frequency | $f_{Resp}$ | 0.3 Hz |
| Respiratory phase | $\theta_{Resp}$ | 0 |
| Wavelength i = 1 ... N AC peak amplitude | $I_{\lambda_i}^{AC}$ | 0.5 max_value |
| Wavelength i = 1 ... N AC peak location | $pos_{\lambda_i}^{AC}$ | Corresponding FFT bin to 1 Hz |
| Wavelength i = 1 ... N DC | $I_{\lambda_i}^{DC}$ | 0.5 max_value |
| Wavelength i = 1 ... N p2p amplitude | $I_{\lambda_i}^{p2p}$ | 1 ADC read |
| Wavelength i = 1 ... N rise time | $\tau_{\lambda_i}^{rise}$ | 0.1 sec |
| Wavelength i = 1 ... N Significance coefficient | $c_{\lambda_i}$ | 1 |
| Wavelength i = 1 ... N HRV | $T_{\lambda_i}^{HRV}$ | 1 sec |
| Best Ratio pH | $BR_{pH}$ | 2 |
| Best Ratio pCO2 | $BR_{pCO2}$ | 3 |
| Best Ratio pHCO3- | $BR_{pHCO3^-}$ | 4 |
| Acceleration magnitude | $I_{move}$ | 0 |
| GPS velocity | $|v|_{GPS}$ | 0 |
| GPS altitude | $|alt|_{GPS}$ | 0 |
| GPS acceleration | $|a|_{GPS}$ | 0 |
| GPS incline | $|incline|_{GPS}$ | 0 |
| Restfulness | Rest | 0 |
| Hydration | Hyd | 0 |
| Systolic Blood Pressure | SBP | 120 mmHg |
| Diastolic Blood Pressure | DBP | 80 mmHg |
| End tidal CO2 | ETCO2 | 40 mmHg |
| Blood Carbon Monoxide | SpCO | 0% |

Table 2 lists one or more parameters for y(n) as well as their initial value in some embodiments:

TABLE 2

| Parameter | Symbol | Initial |
|---|---|---|
| Blood pH | pH | 7.35 |
| Blood PCO2 | $pCO_2$ | 24 mmol |
| Blood PO2 | $pO_2$ | 24 mmol |
| Blood PHCO3- | $pHCO_3^-$ | 24 mmol |
| Blood Glucose | $pC_6H_{12}O_6$ | 3 mmol |
| Cardiac Frequency | $f_{HR}$ | 1 |
| Point Blood Pressure | $P_{Point}$ | 1 |
| Respiratory Frequency | $f_{Resp}$ | 0.3 |
| GPS velocity | $|v|_{GPS}$ | 0 |
| GPS altitude | $|alt|_{GPS}$ | 0 |
| GPS acceleration | $|a|_{GPS}$ | 0 |
| GPS incline | $|incline|_{GPS}$ | 0 |

Table 3 lists the state space model F(X(n)) between the parameters listed in Table 1 and Table 2 in some embodiments, where the energy wavelengths comprise 880 nm, 631 nm, 1450 nm, and 1550 nm:

TABLE 3

| Name | Symbol | Equation |
|---|---|---|
| Cardiac frequency | $f_{HR}$ | $\text{bin\_to\_freq}\left(\dfrac{\Sigma c_{\lambda_i} pos_{\lambda_i}^{AC}}{\Sigma c_{\lambda_i}}\right)$ |
| Cardiac phase | $\theta_{HR}$ | $\theta_{HR}(n-1) + f_s^{-1} * \omega^* \in [\omega\_\min, \omega\_\max]$ |
| Cardiac harmonic amplitude | $I_{Harmonic}^{HR}$ | $\dfrac{\Sigma c_{\lambda_i} I_{\lambda_i}^{p2p}}{\Sigma c_{\lambda_i}}$ |
| Cardiac Pulse Pressure | $P_{HR}$ | $\left(\dfrac{\Sigma c_{\lambda_i} \tau_{\lambda_i}^{rise}}{\Sigma c_{\lambda_i}}\right)^{\wedge} -1$ |
| Point Blood Pressure | $P_{Point}$ | $\tau_{\lambda_1}^{rise^{-1}}$ |
| Respiratory frequency | $f_{Resp}$ | 3) Respiratory and Heart Rate State Models: The fluctuations in the respiratory rate $\omega_r(n)$ and fluctuations in the heart rate $\omega_{ca}(n)$ that are not due to RSA are both modeled as a first-order autoregressive process with a mean and mild nonlinearity that limit the frequencies to know physiologic ranges<br><br>$\omega_r(n+1) = \overline{\omega}_r + \alpha_r \{s_r[\omega_r(n)] - \overline{\omega}_r\} + u_{\omega_r}(n)$ (15)<br>$\omega_{ca}(n+1) = \overline{\omega}_c + \alpha_c \{s_c[\omega_{ca}(n)] - \overline{\omega}_c\} + u_{\omega_{ca}}(n)$ (16)<br><br>where $\overline{\omega}_r$ and $\overline{\omega}_c$ are the a priori estimates of the expected respiratory and cardiac frequencies, respectively; $\alpha_r$ and $\alpha_c$ control the bandwidth of the frequency fluctuations; and $u_{\omega_r}(n)$ and $u_{\omega_{ca}}(n)$ are white noise processes that model the random variation in the respiratory and cardiac frequencies, respectively. The instantaneous respiratory and heart rates in units of Hz are then<br><br>$f_r(n) = \dfrac{1}{2\pi T_s} s_r[\omega_r(n)]$ (17)<br><br>$f_c(n) = \dfrac{1}{2\pi T_s} s_c[\omega_c(n)].$ (18) |
| Respiratory phase | $\theta_{Resp}$ | $\theta_{Resp}(n-1) + f_s^{-1} * \omega^*$, where $\omega^* \in [\omega\_\min, \omega\_\max]$ |
| $\lambda$ = 880 nm AC peak | $I_{\lambda_i}^{AC}$ | From FFT |

TABLE 3-continued

| Name | Symbol | Equation |
|---|---|---|
| $\lambda$ = 880 nm DC | $pos_{\lambda_i}^{AC}$ | From FFT |
| $\lambda$ = 880 nm p2p amplitude | $I_{\lambda_i}^{DC}$ | From Waveform analysis |
| $\lambda$ = 880 nm rise time | $I_{\lambda_i}^{P2p}$ | From Waveform analysis |
| $\lambda$ = 880 nm signal trend | $\tau_{\lambda_i}^{rise}$ | From Waveform analysis |
| $\lambda$ = 880 nm Significance coefficient | $c_{\lambda_i}$ | From Waveform analysis |
| $\lambda$ = 880 nm HRV | $T_{\lambda_i}^{HRV}$ | From Waveform analysis |
| $\lambda$ = 631 nm AC peak | $I_{\lambda_i}^{AC}$ | From Fast Fourier Transformation ("FFT") |
| $\lambda$ = 631 nm DC | $pos_{\lambda_i}^{AC}$ | From FFT |
| $\lambda$ = 631 nm p2p amplitude | $I_{\lambda_i}^{DC}$ | From Waveform analysis |
| $\lambda$ = 631 nm rise time | $I_{\lambda_i}^{P2p}$ | From Waveform analysis |
| $\lambda$ = 631 nm signal trend | $\tau_{\lambda_i}^{rise}$ | From Waveform analysis |
| $\lambda$ = 631 nm Significance coefficient | $c_{\lambda_i}$ | From Waveform analysis |
| $\lambda$ = 631 nm HRV | $T_{\lambda_i}^{HRV}$ | From Waveform analysis |
| $\lambda$ = 1450 nm AC peak | $I_{\lambda_i}^{AC}$ | From FFT |
| $\lambda$ = 1450 nm DC | $pos_{\lambda_i}^{AC}$ | From FFT |
| $\lambda$ = 1450 nm p2p amplitude | $I_{\lambda_i}^{DC}$ | From Waveform analysis |
| $\lambda$ = 1450 nm rise time | $I_{\lambda_i}^{P2p}$ | From Waveform analysis |
| $\lambda$ = 1450 nm signal trend | $\tau_{\lambda_i}^{rise}$ | From Waveform analysis |
| $\lambda$ = 1450 nm Significance coefficient | $c_{\lambda_i}$ | From Waveform analysis |
| $\lambda$ = 1450 nm HRV | $T_{\lambda_i}^{HRV}$ | From Waveform analysis |
| $\lambda$ = 1550 nm AC peak | $I_{\lambda_i}^{AC}$ | From FFT |
| $\lambda$ = 1550 nm DC | $pos_{\lambda_i}^{AC}$ | From FFT |
| $\lambda$ = 1550 nm p2p amplitude | $I_{\lambda_i}^{DC}$ | From Waveform analysis |
| $\lambda$ = 1550 nm rise time | $I_{\lambda_i}^{P2p}$ | From Waveform analysis |
| $\lambda$ = 1550 nm signal trend | $\tau_{\lambda_i}^{rise}$ | From Waveform analysis |
| $\lambda$ = 1550 nm Significance coefficient | $c_{\lambda_i}$ | From Waveform analysis |
| $\lambda$ = 1550 nm HRV | $T_{\lambda_i}^{HRV}$ | From Waveform analysis |
| Best Ratio pH | $BR_{pH}$ | Device Calibration |
| Best Ratio pCO2 | $BR_{pCO2}$ | Device Calibration |
| Best Ratio pHCO3− | $BR_{pHCO3-}$ | Device Calibration |
| Acceleration magnitude | $I_{move}$ | From Accelerometer |
| GPS velocity | $|v|_{GPS}$ | From GPS |
| GPS altitude | $|alt|_{GPS}$ | From GPS |
| GPS acceleration | $|a|_{GPS}$ | From GPS |
| GPS incline | $|incline|_{GPS}$ | From GPS |

Table 4 Lists $Y(n)=H(x(n))$:

TABLE 4

| Name | Symbol | Equation |
|---|---|---|
| Blood pH | pH | $6.1 + \log\left(\dfrac{pHCO_3^-}{0.03 vCO_2}\right)$ |
| Blood PCO2 | pCO$_2$ | $\dfrac{\epsilon_{Hb}^{CO_2} - \epsilon_{Hb}^{Hb} * I_{\lambda_{CO_2}}^{AC} * I_{\lambda_1}^{DC} / \left(I_{\lambda_1}^{AC} * I_{\lambda_{CO_2}}^{DC}\right)}{\epsilon_{Hb}^{CO_2} - \epsilon_{CO_2}^{CO_2} + \left(\epsilon_{CO_2}^{Hb} - \epsilon_{Hb}^{Hb}\right) * I_{\lambda_{CO_2}}^{AC} * I_{\lambda_1}^{DC} / \left(I_{\lambda_1}^{AC} * I_{\lambda_{CO_2}}^{DC}\right)}$ |
| Blood PO2 | pO$_2$ | $\dfrac{\epsilon_{Hb}^{O_2} - \epsilon_{Hb}^{Hb} * I_{\lambda_{O_2}}^{AC} * I_{\lambda_1}^{DC} / \left(I_{\lambda_1}^{AC} * I_{\lambda_{O_2}}^{DC}\right)}{\epsilon_{Hb}^{O_2} - \epsilon_{O_2}^{O_2} + \left(\epsilon_{O_2}^{Hb} - \epsilon_{Hb}^{Hb}\right) * I_{\lambda_{O_2}}^{AC} * I_{\lambda_1}^{DC} / \left(I_{\lambda_1}^{AC} * I_{\lambda_{O_2}}^{DC}\right)}$ |
| Blood PHCO3– | pHCO$_3^-$ | $\dfrac{\epsilon_{Hb}^{HCO_3^-} - \epsilon_{Hb}^{Hb} * I_{\lambda_{HCO_3^-}}^{AC} * I_{\lambda_1}^{DC} / \left(I_{\lambda_1}^{AC} * I_{\lambda_{HCO_3^-}}^{DC}\right)}{\epsilon_{Hb}^{HCO_3^-} - \epsilon_{HCO_3^-}^{HCO_3^-} + \left(\epsilon_{HCO_3^-}^{Hb} - \epsilon_{Hb}^{Hb}\right) * I_{\lambda_{HCO_3^-}}^{AC} * I_{\lambda_1}^{DC} / \left(I_{\lambda_1}^{AC} * I_{\lambda_{HCO_3^-}}^{DC}\right)}$ |
| Blood Glucose | pC$_6$H$_{12}$O$_6$ | As above |
| Cardiac Frequency | $f_{HR}$ | As in f(x(n)) |
| Point Blood Pressure | $P_{Point}$ | As in f(x(n)) |
| Respiratory Frequency | $f_{Resp}$ | As in f(x(n)) |
| GPS velocity | $|v|_{GPS}$ | As in f(x(n)) |
| GPS altitude | $|alt|_{GPS}$ | As in f(x(n)) |
| GPS acceleration | $|a|_{GPS}$ | As in f(x(n)) |
| GPS incline | $|incline|_{GPS}$ | As in f(x(n)) |

As illustrated in Tables 3 and 4, by generating energy at different wavelengths, one or more blood metrics may be determined from the detected energy. For example, cardiac frequency, cardiac phase, cardiac harmonic amplitude, cardiac pulse pressure, point blood pressure, respiratory rate or frequency, respiratory phase, blood pH, blood pCO$_2$, blood pHCO$_{3-}$, or blood glucose, may be determined.

In step 310, the blood metrics measurement apparatus provides the generated one or more signals for respiratory rate calculation. In some embodiments, a communication module (e.g., communication module 1008) provides one or more signals to, for example, a respiratory rate calculation system and/or user device.

Table 5 lists the state space model $F(X(n))$ between the parameters listed in Table 1 and Table 2 in some other embodiments, where the energy wavelengths comprise 880 nm, 631 nm, 450 nm, and 550 nm:

TABLE 5

| Name | Symbol | Equation |
|---|---|---|
| Cardiac frequency | $f_{HR}$ | $\text{bin\_to\_freq}\left(\dfrac{\Sigma c_{\lambda_i} pos_{\lambda_i}^{AC}}{\Sigma c_{\lambda_i}}\right)$ |
| Cardiac phase | $\theta_{HR}$ | $\theta_{HR}(n-1) + f_s^{-1} * \omega^* \in [\omega\_\min, \omega\_\max]$ |
| Cardiac harmonic amplitude | $I_{Harmonic}^{HR}$ | $\dfrac{\Sigma c_{\lambda_i} I_{\lambda_i}^{p2p}}{\Sigma c_{\lambda_i}}$ |
| Cardiac Pulse Pressure | $P_{HR}$ | $\left(\dfrac{\Sigma c_{\lambda_i} \tau_{\lambda_i}^{rise}}{\Sigma c_{\lambda_i}}\right)^{\wedge}-1$ |
| Point Blood Pressure | $P_{Point}$ | $\tau_{\lambda_1}^{rise^{-1}}$ |
| Respiratory frequency | $f_{Resp}$ | 3) Respiratory and Heart Rate State Models: The fluctuations in the respiratory rate $\omega_r(n)$ and fluctuations in the heart rate $\omega_{ca}(n)$ that are not due to RSA are both modeled as a first-order autoregressive process with a mean and mild nonlinearity that limit the frequencies to know physiologic ranges<br>$\omega_r(n+1) = \overline{\omega}_r + \alpha_r \{s_r [\omega_r(n)] - \overline{\omega}_r\} + u_{\omega_r}(n)$ (15)<br>$\omega_{ca}(n+1) = \overline{\omega}_c + \alpha_c \{s_c [\omega_{ca}(n)] - \overline{\omega}_c\} + u_{\omega_{ca}}(n)$ (16)<br>where $\overline{\omega}_r$ and $\overline{\omega}_c$ are the a priori estimates of the expected respiratory and cardiac frequencies, respectively; $\alpha_r$ and $\alpha_c$ control the bandwidth of the frequency fluctuations; and $u_{\omega_r}(n)$ and $u_{\omega_{ca}}(n)$ are white noise processes that model the random variation in the respiratory and cardiac frequencies, respectively. The instantaneous respiratory and heart rates in units of Hz are then |

TABLE 5-continued

| Name | Symbol | Equation |
|---|---|---|
| | | $f_r(n) = \frac{1}{2\pi T_s} s_r[\omega_r(n)]$  (17) |
| | | $f_c(n) = \frac{1}{2\pi T_s} s_c[\omega_c(n)].$  (18) |
| Respiratory phase | $\theta_{Resp}$ | $\theta_{Resp}(n-1) + f_s^{-1} * \omega^*$, where $\omega^* \in [\omega\_min, \omega\_max]$ |
| $\lambda = 880$ nm AC peak | $I_{\lambda_i}^{AC}$ | From FFT |
| $\lambda = 880$ nm DC | $pos_{\lambda_i}^{AC}$ | From FFT |
| $\lambda = 880$ nm p2p amplitude | $I_{\lambda_i}^{DC}$ | From Waveform analysis |
| $\lambda = 880$ nm rise time | $I_{\lambda_i}^{p2p}$ | From Waveform analysis |
| $\lambda = 880$ nm signal trend | $\tau_{\lambda_i}^{rise}$ | From Waveform analysis |
| $\lambda = 880$ nm Significance coefficient | $c_{\lambda_i}$ | From Waveform analysis |
| $\lambda = 880$ nm HRV | $T_{\lambda_i}^{HRV}$ | From Waveform analysis |
| $\lambda = 631$ nm AC peak | $I_{\lambda_i}^{AC}$ | From Fast Fourier Transformation ("FFT") |
| $\lambda = 631$ nm DC | $pos_{\lambda_i}^{AC}$ | From FFT |
| $\lambda = 631$ nm p2p amplitude | $I_{\lambda_i}^{DC}$ | From Waveform analysis |
| $\lambda = 631$ nm rise time | $I_{\lambda_i}^{p2p}$ | From Waveform analysis |
| $\lambda = 631$ nm signal trend | $\tau_{\lambda_i}^{rise}$ | From Waveform analysis |
| $\lambda = 631$ nm Significance coefficient | $c_{\lambda_i}$ | From Waveform analysis |
| $\lambda = 631$ nm HRV | $T_{\lambda_i}^{HRV}$ | From Waveform analysis |
| $\lambda = 450$ nm AC peak | $I_{\lambda_i}^{AC}$ | From FFT |
| $\lambda = 450$ nm DC | $pos_{\lambda_i}^{AC}$ | From FFT |
| $\lambda = 450$ nm p2p amplitude | $I_{\lambda_i}^{DC}$ | From Waveform analysis |
| $\lambda = 450$ nm rise time | $I_{\lambda_i}^{p2p}$ | From Waveform analysis |
| $\lambda = 450$ nm signal trend | $\tau_{\lambda_i}^{rise}$ | From Waveform analysis |
| $\lambda = 450$ nm Significance coefficient | $c_{\lambda_i}$ | From Waveform analysis |
| $\lambda = 450$ nm HRV | $T_{\lambda_i}^{HRV}$ | From Waveform analysis |
| $\lambda = 550$ nm AC peak | $I_{\lambda_i}^{AC}$ | From FFT |
| $\lambda = 550$ nm DC | $pos_{\lambda_i}^{AC}$ | From FFT |
| $\lambda = 550$ nm p2p amplitude | $I_{\lambda_i}^{DC}$ | From Waveform analysis |
| $\lambda = 550$ nm rise time | $I_{\lambda_i}^{p2p}$ | From Waveform analysis |
| $\lambda = 550$ nm signal trend | $\tau_{\lambda_i}^{rise}$ | From Waveform analysis |
| $\lambda = 550$ nm Significance coefficient | $c_{\lambda_i}$ | From Waveform analysis |
| $\lambda = 550$ nm HRV | $T_{\lambda_i}^{HRV}$ | From Waveform analysis |
| Best Ratio pH | $BR_{pH}$ | Device Calibration |
| Best Ratio pCO2 | $BR_{pCO2}$ | Device Calibration |
| Best Ratio pHCO3− | $BR_{pHCO3-}$ | Device Calibration |
| Acceleration magnitude | $I_{move}$ | From Accelerometer |
| GPS velocity | $|v|_{GPS}$ | From GPS |
| GPS altitude | $|alt|_{GPS}$ | From GPS |
| GPS acceleration | $|a|_{GPS}$ | From GPS |
| GPS incline | $|incline|_{GPS}$ | From GPS |

Figure 4:
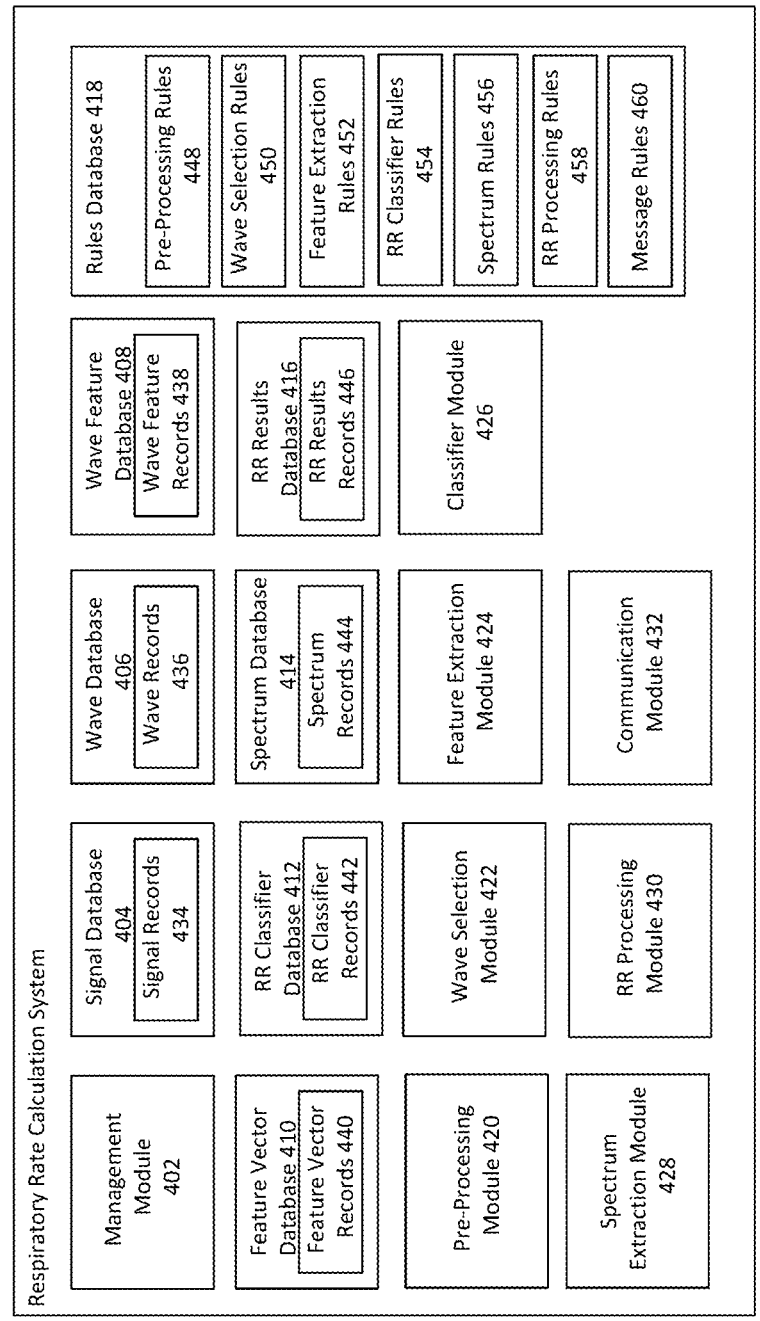
FIG. 4 depicts a block diagram of a respiratory rate calculation system according to some embodiments.

FIG. 4 depicts a block diagram of a respiratory rate calculation system 400 according to some embodiments. Generally, the respiratory rate calculation system 400 may be configured to calculate respiratory rate values of a user. The respiratory rate calculation system 400 may also store calculated respiratory rate values (e.g., for health tracking, etc.), and communicate with other systems of the system 400 and environment. In some embodiments, the respiratory rate calculation system 400 includes a management module 402, a signal database 404, a wave database 406, a wave feature database 408, a feature vector database 410, a respiratory rate classifier database 412, a spectrum database 414, a respiratory rate results database 416, a rules database 418, a pre-processing module 420, a wave selection module 422, a feature extraction module 424, a respiratory rate processing module 430, and a communication module 432.

The management module 402 may be configured to manage (e.g., create, read, update, delete, or access) signal records 434 stored in the signal database 404, wave records 436 stored in the wave database 406, wave feature records 438 stored in the wave feature database 408, feature vector records 440 stored in the feature vector database 410, respiratory rate classifier records 442 stored in the respiratory rate classifier database 412, spectrum records 444 stored in spectrum database 414, respiratory rate result records 446 stored in the respiratory rate results database 416, and/or rules 448-460 stored in rules database 418. The management module 402 may perform these operations manually (e.g., by an administrator interacting with a GUI) and/or automatically (e.g., by one or more of the modules 420-430). In some embodiments, the management module 402 comprises a library of executable instructions which are executable by a processor for performing any of the aforementioned management operations. The databases 404-418 may be any structure and/or structures suitable for storing the records 434-446 and/or the rules 448-460 (e.g., an active database, a relational database, a table, a matrix, an array, a flat file, and the like).

The signal records 434 may include a variety of signals, along with associated metadata. For example, the signals may comprise multichannel optical and/or non-optical signals. In some embodiments, the metadata may include information obtained from the signals, such as heart rate(s) of an associated user. For example, the signal records 434 may store some or all of the following information:

Signal(s) Identifier: Identifier that identifies the stored signal(s).

Signal(s): one or more signals. The signals may be raw signals (e.g., as detected by the associated respiratory rate measurement apparatus), filtered or pre-processed signals (e.g., to remove noise from the signals), and/or normalized signal values (e.g., between 0-1). An example "noisy" (i.e., unfiltered) PPG signal and an example filtered PPG signal are shown in FIG. 19. It will be appreciated that, a "signal," such as a PPG signal or pressure pulse signal, generally refers to a filtered signal, although in some embodiments, it may also refer to an unfiltered signal instead of, or in addition to, the filtered signal.

Set(s) of Waves: one or more sets of waves of a predetermined time series or window (e.g., 30 seconds) of the signal. The waves may include raw waves, filtered waves, and/or normalized wave values (e.g., between 0-1).

Apparatus Identifier: Identifier that identifies the blood metrics measurement apparatus that generated the signals.

User Account Identifier: Identifier that identifies a user account associated with the blood metrics measurement apparatus that generated the signals.

Metadata: Metadata obtained from the signals, such as heart rate or other biometric data. The metadata may also include other information of the user, such as gender, age, height, weight, skin color (e.g., obtained from the user's account information). Such metadata values may be used by the respiratory rate processing module 430 (discussed below) to facilitate calculation of respiratory rate values. In some embodiments, metadata values may be provided to an respiratory rate classifier (discussed below) via sets of feature vectors (discussed below) and/or be provided separately to the classifier.

The wave records 436 may include sets of waves of a signal (e.g., a signal stored in the signal database 404). In some embodiments, the wave records 436 may store some or all of the following information:

Signal Identifier: Identifier that identifies an associated signal.

Wave Identifier(s): Identifiers for waves of the associated signal.

Apparatus Identifier: Identifier that identifies the blood metrics measurement apparatus that generated the signals.

User Account Identifier: Identifier that identifies a user account associated with the blood metrics measurement apparatus that generated the signals.

The wave feature records 438 may include wave features of associated waves of a signal. For example, wave features may include wave peaks, wave valleys, wave edges, optical ratios, heart rate, signal level and range, signal metrics, energy in different frequency ranges, and/or the like. In some embodiments, the wave feature records 438 may store some or all of the following information:

Signal Identifier: Identifier that identifies an associated signal.

Wave Identifier(s): Identifiers for the subsets of waves of the associated signal.

Wave Features: one or more features obtained from the waves. The wave features may be stored as normalized wave values (e.g., between 0-1).

Apparatus Identifier: Identifier that identifies the blood metrics measurement apparatus that generated the signals.

User Account Identifier: Identifier that identifies a user account associated with the blood metrics measurement apparatus that generated the signals.

The feature vector records 440 may include sets of features generated based on the wave features of associated waves of a signal. In some embodiments, the feature vector records 440 may store some or all of the following information:

Signal Identifier: Identifier that identifies an associated signal.

Wave Identifier(s): Identifier(s) for wave(s) of the associated signal.

Set(s) of Feature Vectors: one or more sets of feature vectors, each feature vector comprising features extracted from a wave. The values of a feature vector may include measurement values and metric values. For example, the measurement values may correspond to amplitude or location points of a particular wave, and the metric values may be generated from metric functions that use at least one of the measurement values.

The values of a feature vector may comprise normalized values (e.g., between 0-1).

Apparatus Identifier: Identifier that identifies the blood metrics measurement apparatus that generated the signals.

User Account Identifier: Identifier that identifies a user account associated with the blood metrics measurement apparatus that generated the signals.

The respiratory rate classifier records 442 may include one or more respiratory rate classifiers. In some embodiments, respiratory rate classifiers may comprise a machine learning algorithm (e.g., a Support Vector Machine (SVM) or Random Forests algorithm). In some embodiments, respiratory rate classifiers may facilitate determining filter parameters for filtering signals during pre-processing. The classifiers may include various types of respiratory rate classifiers. For example, a first type may be a "non-specific" classifier which does not require calibration in order to be used to calculate respiratory rate values. A second type may be a "specific" classifier which requires calibration in order to be used to calculate respiratory rate values. For example, classifiers of the second type may require information about the user, such age, weight, height, gender, skin color, and/or the like. In some embodiments, the respiratory rate records 442 may store some or all of the following information:

Classifier Identifier: Identifies a respiratory rate classifier.

Classifier Type: Identifies a type of classifier (e.g., non-specific or specific).

Classifier Parameters: Various classifier parameters used to determine filter parameters for filtering signals during pre-processing based on feature vectors.

Apparatus Identifier(s): Identifier(s) that identify one or more blood metrics measurement apparatus' using the respiratory rate classifier.

User Account Identifier(s): Identifier(s) that identify one or more user account(s) associated with the blood metrics measurement apparatus that use the respiratory rate classifier.

The spectrum records 436 may include determined or estimated spectrums of a signal (e.g., a signal stored in the signal database 404). In some embodiments, the spectrum records 436 may store some or all of the following information:

Signal Identifier: Identifier that identifies an associated signal.

Spectrum Identifier(s): Identifiers for spectrums of the associated signal.

Apparatus Identifier: Identifier that identifies the blood metrics measurement apparatus that generated the signals.

User Account Identifier: Identifier that identifies a user account associated with the blood metrics measurement apparatus that generated the signals.

The respiratory rate results records 446 may include one or more calculated respiratory rate values. In some embodiments, the respiratory rate results records 446 may store some or all of the following information:

Respiratory Rate Result Identifier: Identifies a set of one or more calculated respiratory rate values.

Respiratory Rate Values: one or more calculated respiratory rate values.

Date: A date and/or time the respiratory rate was calculated.

Messages: Message identifier and/or messages generated based on the calculated respiratory rate values.

Signal Identifier: Identifier that identifies an associated signal.

Wave Identifier(s): Identifiers for the waves of the associated signal.

Feature Vectors Identifier(s): Identifiers for the one or more sets of feature vectors used to calculate select, configure, and/or train an associated classifier.

Apparatus Identifier: Identifier that identifies the blood metrics measurement apparatus that generated the signals.

User Account Identifier: Identifier that identifies a user account associated with the blood metrics measurement apparatus that generated the signals.

Pre-Processing Rules 448

The pre-processing rules 448 define attributes and/or functions for filtering signals. For example, a signal may be corrupted with noise from various sources (e.g., high frequency ambient noise, electronic noise, and the like). In some embodiments, the signal may be signal from a photodiode, output of a pressure sensor, output of an accelerometer, output of a gyroscope, or the like. The signal may be filtered to remove corrupting noise, as well as enhance a strength of the signal.

Typically, respiration is a slowly varying signal, often not more than 40 BPM (or 0.67 Hz), and the signal may need to be measured over longer durations (e.g., relative to pulse rate, which can usually be measured at an interval of 1 second) before a respiratory rate can be determined. For example, a 30 second window may be used over a PPG window, sampled upwards of 50 Hz. In some embodiments, the respiration signal may include information less than 1 Hz, and it can be decimated up to 2 Hz before processing (e.g., for computational efficiency). In some embodiments, pre-processing may apply a high pass filter (e.g., at cut-off 0.1 Hz) to eliminate, reduce, remove and/or attenuate (or, collectively, "remove") low frequency drift inherit to signals. In some embodiments, the high pass filter may have a narrow transition band (e.g., 0.05 Hz). In some embodiments, Savitzky-Golay filtering may be both computationally efficient and effective in eliminating low-frequency drift. In some embodiments, if the filter order is high, it may also eliminate some useful high frequency components of the signal. In some embodiments, a classifier may be used to determine appropriate or optimized filter parameters.

In some embodiments, filter parameters are determined based on a true respiration rate. Accordingly, a classifier may be generated or trained to identify categories of respiration rate (e.g., low and high) based on signal data. In some embodiments, the classifier may be applied to determine filter parameters for filtering during pre-processing (e.g., using low pass, high pass, or other filters).

The pre-processing module 420 may be configured to execute the pre-processing rules 448. Thus, for example, the pre-processing module 420, using some or all of the associated signals and/or values stored in the signal records 434, may filter signals and store the resulting filtered signals. The wave database 406 may be configured to store the signals filtered by the pre-processing module 420.

Wave Selection Rules 450

The wave selection rules 450 define attributes and/or functions for selecting (or, "extracting") one or more waves or sets of waves from a signal. For example, waves of a predetermined time series (e.g., 30 seconds) may be extracted from a signal. The wave selection module 422 may be configured to execute the wave selection rules 442. Thus, for example, the wave selection module 422, using some or all of the associated waves and/or values stored in the signal records 434, may extract waves over or from a predetermined time series. The wave database 406 may be configured to store the extracted waves.

Feature Extraction Rules 452

The feature extraction rules 452 define attributes and/or functions for identifying (or, "extracting") features of waves of a signal. In some embodiments, features may be concatenated or combined to form feature vectors. Once the features are extracted, they may be used with ground truth data to train respiratory rate classifiers. Examples features are described below, although it will be appreciated that like the other examples in this paper, these are non-limiting examples.

In some embodiments, features may include, but are not limited to, pulse transit time (PTT) features, reflection features, signal level and range features, signal metric features, optical ratio features, heart rate features, wave width and derivative features, user information features, and/or pressure features. PTT features may include a transit time feature, joint entropy feature, and/or wave type feature. Pulse transit time may be measured as the time taken for the pulse pressure wave to propagate along the length of the arterial tree. For example, this may be the difference in time between the onset of the R-wave on ECG, and the pulse wave peak on the finger. In other embodiments, the transit time may be measured as the time taken for blood to travel from one LED-PD system to another LED-PD system, which may be separated from each other by a predetermined distance (e.g., 5 mm). Sampling at a very high rate (>2 KHz) may help resolve features in both LED-PD systems. In some embodiments, the transit time may be measured as (1) the distance between the valleys in the corresponding waves in respective LED-PD systems at the start of the systolic cycle, and/or (2) the distance between the peaks in first derivatives between the two LED-PD systems. The transit time may be expressed in any units (e.g., milliseconds).

The joint entropy feature may be a measurement of similarity between fast channels of respective LED-PD systems. High pulse pressure may correlate with low entropy or high mutual information shared between the fast LED channels. The joint entropy feature may be expressed in bytes.

Wave type features may include different types of waves. For example, different types of waves may include slow type waves and fast type waves. The wave types feature may quantify a relative position of the systolic peak within the wave (0<WaveType<1) for each of the fast channels in respective LED-PD systems, where small values correspond to a slow type waves and larger values correspond to fast type waves.

A pulse decomposition may track a pulse pressure wave. As the pressure wave travels in the arterial systems, it may encounter branching points where the diameter of arteries may decrease rapidly. The pressure wave may bounce on such branching points and send reflection waves in different (e.g., opposite) directions. In some embodiments, the original pressure wave plus the reflections may form the observed pressure pulse, which in turn may be observed in a signal (e.g., PPG signal). Multiple reflections (e.g., four reflections), in some embodiments, may be used to identify multiple features and amplitudes (e.g., four features and four amplitudes). The time of occurrence of the systolic peak from the start of the systolic cycle (i.e., systolic peak time) may also be included as a feature. A ratio between the second derivatives at the bottom and peak of the systolic cycle may be used as a feature. This feature has been correlated with arterial stiffness. Ten features may be individually identified for each LED channel.

The signal level and range features comprise the mean value and range of a signal (e.g., PPG signal) determined for each of the channels. In some embodiments, the signal metrics features include Hjorth parameters, perfusion, kurtosis, and energy. Hjorth parameters may describe activity, mobility and complexity of the signal, and are commonly used tools in EEG analysis. Perfusion may be measured as the ratio between the AC and DC components of the signal (i.e., the range of the signal and the mean). Kurtosis may be measured over the signal analysis window. Energy may the variance of the signal measured over the analysis window. In some embodiments, optical ratio features may be calculated as the ratio of the range of the LEDs (measured in pairs across wavelengths) after normalization of the respective signals, and heart rate features may be an actual user heart rate or a default heart rate.

In various embodiments, if two LEDs at the same wavelength are positioned at different locations of the same artery, a phase shift may be obtained between the measured signals (e.g., due to blood flow). This may facilitate calculation of pulse wave velocity (PWV) and/or pulse transit time (PTT), both of which may be included in a feature vector, and/or otherwise provided to the empirical respiratory rate model used to calculate respiratory rate values.

The user information features such as a user's gender, age, skin color, height and/or weight may be included in a feature vector, and/or otherwise provided to the empirical respiratory rate model used to calculate respiratory rate values. In some embodiments, pressure features may include the mean value of the pressure signal over the analysis window (or "baseline mean") and range of the pressure signal over the analysis window (or, "AC").

The feature extraction module 424 may be configured to execute the feature extraction rules 452. Thus, for example, the feature extraction module 422, using some or all of the associated subsets of waves and/or values stored in the wave records 436, may identify one or more feature of the waves within the subsets of waves, and generate corresponding sets of feature vectors. The wave feature database 408 may be configured to store the wave features identified by the feature extraction module 424, and the feature vector database 410 may be configured to store the generated sets of feature vectors.

Respiratory Rate Classifier Rules 454

The respiratory rate classifier rules 454 define attributes and/or functions for generating, selecting, and/or training respiratory rate classifiers for determining filter parameters for use during signal pre-processing. In some embodiments, the respiratory rate classifier rules 454 may define input values for a respiratory rate classifiers. For example, input values may comprises sets of features vectors and ground truth data.

In some embodiments, respiratory rate classifiers may be trained using machine learning. For example, features may extracted from individual waves as well as the signal window from which it is extracted. Features may be grouped by optical ratios, heart rate, signal level and range (e.g., mean value, range of signals), signal metrics (e.g., Hjorth parameters, Perfusion, Kurtosis, Interquartile range (IQR)), zero-crossings, and/or energy of spectrum in different frequency ranges. Features from some or all of the groups may be concatenated or combined to form feature vectors, and may be used for classifier learning and feature selection processes. In some embodiments, a particular subset of features may be used (e.g., Hjorth parameters, IQR and the energy measured from the high frequency range of the spectrum) to form feature vectors.

In some embodiments, ground truth data may be collected (e.g., by a Masimo device) and stored, and the wave feature vectors may be used to train a classifier (e.g., a Support Vector Machine (SVM)). Performance metrics may be used to assess a particular classifier and select which classifier to use for particular situations and environments. For example, the performance metrics may include a confusion matrix, receiver operation curve (ROC), area under curve (AUC), and F-1 score. The trained classifier may be used in conjunction with the respiration rate analysis to determine filter parameters.

The classifier module 426 may be configured to execute the classifier rules 454. For example, the classifier module 422, using one or more classifiers stored in the classifier records 442 and associated ground truth data and feature vectors, may define a set of filter parameters for pre-processing signals (e.g., by the pre-processing module 420).

Spectrum Rules 456

The spectrum rules 456 define attributes and/or functions for extracting (or, "estimating") a spectrum of a signal. Typically, signal based respiration rate estimation techniques typically use a single channel (e.g., one LED and photodetector pair) measurement obtained on a digit (e.g., finger pulse), and the signal is typically acquired under clinical conditions where the user is generally not in a state of motion. Additionally signals measured on the finger may be much stronger relative to signals measured on the wrist. For example, when a user wears a measurement device on the wrist, the signal may be relatively weak (e.g., compared to finger pulse). In some embodiments, the spectrum rules 456 may compensate for weak signals by causing multiple LEDs, configured at the same or different wavelengths, to each produce a signal of the same width concurrently (i.e., time multiplexed). In various embodiments, a pre-processed pressure sensor signal and accelerometer signals may also be used for spectrum estimation (i.e., sensor fusion). The pressure sensors may be less sensitive to motion artifacts than optical sensors, and data fusion may be effective in obtaining more accurate spectrum estimation.

The spectrum rules 456 may define non-parametric and/or parametric spectrum extraction functions for determining the spectrum of the multichannel signal. In some embodiments, non-parametric spectrum extraction estimates power spectral density of a signal over a frequency content of the signal, and may be used to identify key frequencies in periodic signals. Parametric spectrum extraction may use autoregressive modeling that describe a series output as a weighted sum of its previous outputs.

The spectrum module 428 may be configured to execute the spectrum rules 456. Thus, for example, the spectrum module 428, using one or more signals stored in the signal records 434, may extract or estimate a respiratory rate spectrum of a signal.

Respiratory Rate Processing Rules 458

The respiratory rate processing rules 458 define attributes and/or functions for removing signal noise (e.g., motion related noise) and calculating respiratory rate values of a user. In some embodiments, the respiratory rate processing rules 458 may calculate respiratory rates based on a strongest peak with harmonics in the spectrum in noise-free situations. Harmonics may be apparent at integer multiples of the respiratory rate. For example, if true respiratory rate is 3 BPM, then harmonics at 22 BPM and 33 BPM may be detected. These harmonics usually have weaker amplitudes than true respiratory rate and may be detected and distinguished from the respiratory rate peak. Ambient noise and motion related may introduce other peaks stronger than respiratory rate peak (e.g., as shown in FIG. 23) or may amplify high frequency harmonics of respiratory rate. Accordingly, false estimates may be measured.

The respiratory rate processing rules 458 define a temporal filter (e.g., a Kalman filter) to compensate for false estimates. In the some embodiments, the temporal filter may be a linear quadratic estimation that uses a series of noisy measurements and the information related to previous time points, which may produce more precise estimates than can be achieved using a single measurement. The temporal filter may assume the true state at time k may be evolved from the state k−1. For example, the linear formulae of the temporal filter at time k may be $x_k = F_k x_{k-1} + B_k u_k + w_k$, where $F_k$ is the state transition matrix, $B_k$ control-input model, $x_k$ the state matrix, $u_k$ control input and $w_k$ the process noise, drawn from a zero mean multivariate Gaussian distribution with covariance $Q_k$. In some embodiments, ARIMA models or autoregressive (AR) models may be used.

In various embodiments, the temporal filter may comprise $z_k = H_k x_k + v_k$, where $H_k$ is the observation matrix, $z_k$ observation vector, and $v_k$ the measurement noise vector, again drawn from a zero mean multivariate Gaussian distribution with covariance $R_k$. The temporal filter may, in some embodiments, operate in two phases (e.g., a first phase (or, a "predict" phase) and a second phase (or, an "update" phase)). In the predict phase, the state vector and the estimate covariance matrix may be predicted using the state vector from previous time point. In the update phase, the predictions and measurements may be incorporated to calculate a Kalman Gain and update the state vector. In some embodiments, if an observation is not available, the update phase may be skipped and the predict phase may be performed multiple times. Similarly, the update phase may be repeated multiple times if multiple observations are available at time k. In some embodiments, the formulae for the predict and update phases may be as follows:

Predict:

$$\hat{x}_{k|k-1} = F_k \hat{x}_{k-1|k-1} + B_k u_k$$

$$P_{k|k-1} = F_k P_{k-1|k-1} F_k^T + Q_k$$

Update:

$$y_{k|k-1} = z_k - H_k x_{k-1|k-1}$$

$$S_k = H_k P_{k|k-1} H_k^T + R_k$$

$$K_k = P_{k|k-1} H_k^T S_k^{-1}$$

$$\hat{x}_{k|k} = \hat{x}_{k|k-1} + K_k y_k$$

$$P_{k|k} = (I - K_k H_k) P_{k|k-1}$$

The respiratory processing rules 458 may define a non-linear model adapted for the measurement and state-space models (e.g., an extended Kalman filter).

In some embodiments, noise statistics of the measurements, $R_k$, may be provided to the temporal filter. For example, a noise reference may be obtained from the estimated spectrum of the measured signals (e.g., by the module 428 executing rules 456). The noise reference may comprise a ratio of the captured harmonic to the next strongest peak after the captured harmonic. The temporal filter may extract some or all of the possible peaks with harmonics that can correspond to respiration rate. Spurious peaks (e.g., due to motion) may be mistakenly captured by the temporal filter. The rules 458, may compensate using the noise reference and/or one or more previous estimates of the respiration rate scaled by empirically obtained AR coefficients. Accordingly, the true respiration rate peak may be emphasized, while spurious peaks (e.g., due to motion) may be deemphasized.

The respiratory rate processing module 430 may be configured to execute the respiratory rate processing rules 458. Thus, for example, the respiratory rate processing module 430, using a respiratory rate classifier stored in the respiratory rate classifier database 412, along with some or all of the associated sets of feature vectors and/or values stored in the feature vector records 446, may calculate one or more respiratory rate values. The respiratory rate results database 416 may be configured to store the respiratory rate values calculated by the respiratory rate processing module 430.

Message Rules 460

The message rules 460 define attributes and/or functions for generating messages and/or alerts based on respiratory rate values. In some embodiments, the message rules 460 may define rules that cause the respiratory rate calculation system 1206 to provide calculate respiratory rate values to a user. In some embodiments, the message rules 460 may include threshold values and/or conditions that when exceeded and/or satisfied, trigger a message or alert. For example, a threshold value (or value range) and/or threshold condition may be associated with varying respiratory rate levels, and a calculated respiratory rate value which satisfies a corresponding threshold condition or value may trigger a message or alert (e.g., indicating the corresponding respiratory rate level).

In some embodiments, the communication module 432 may be configured to execute the message rules 460. Thus, for example, the communication module 422, using some or all of the respiratory rate values stored in the respiratory rate results records 446, may generate one or more messages. The communication module 432 may be configured to provide those messages to a user.

In some embodiments, the communication module 432 may be configured to send requests to and receive data from one or a plurality of systems. The communication module 432 may send requests to and receive data from a systems through a network or a portion of a network. Depending upon implementation-specific or other considerations, the communication module 432 may send requests and receive data through a connection (e.g., the communication network 908, and/or the communication link 910), all or a portion of which may be a wireless connection. The communication module 432 may request and receive messages, and/or other communications from associated systems.

Figure 5A:
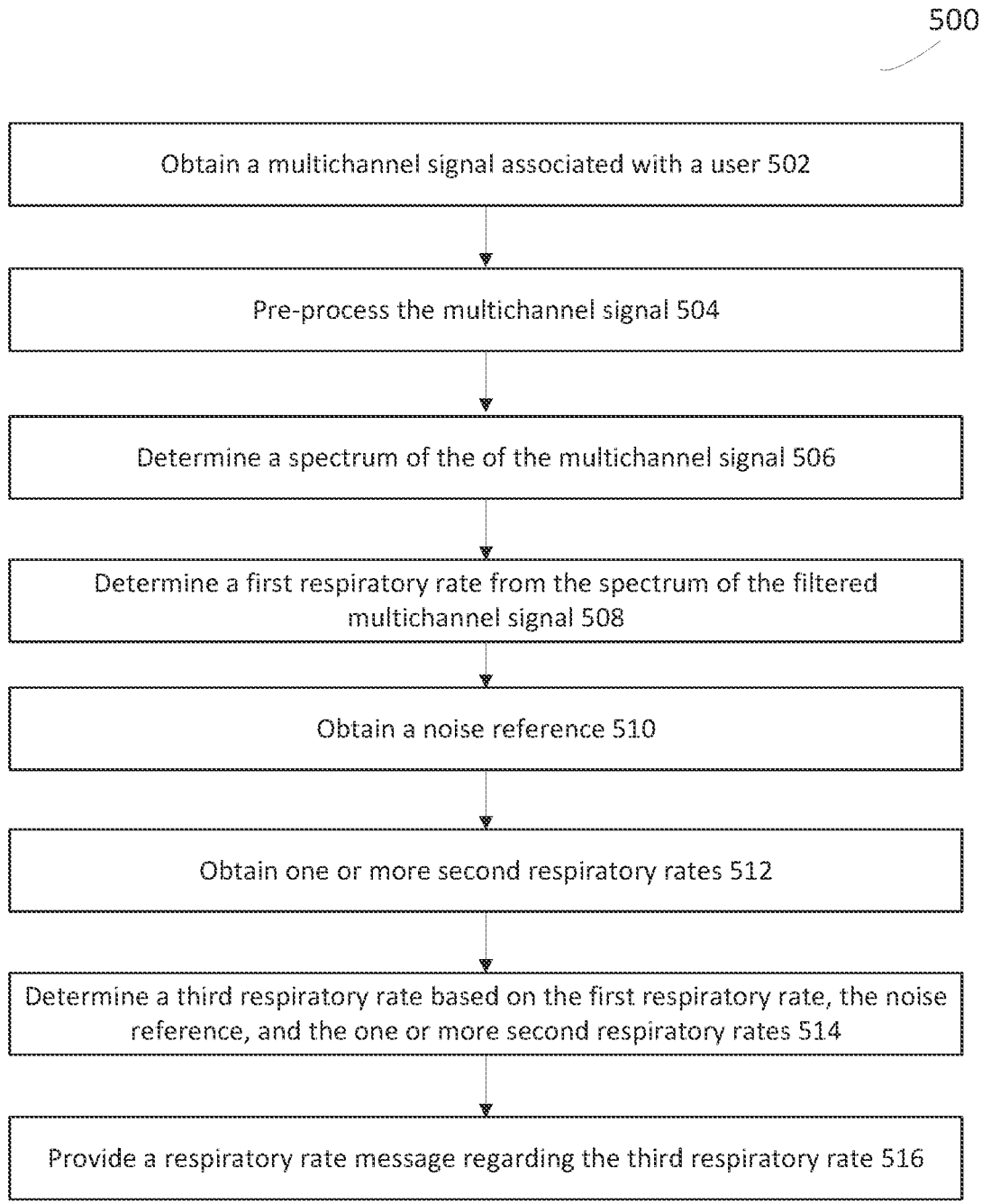
FIG. 5A depicts a flowchart of an example method of operation of a respiratory rate calculation system according to some embodiments.

FIG. 5A depicts a flowchart 500 of an example method of operation of a respiratory rate calculation system according to some embodiments.

In step 502, a respiratory rate calculation system obtains a signal. For example, the signal may comprise a multichannel PPG signal generated from light energy emitted at the same or different wavelengths (e.g., 523 nm, 590 nm, 623 nm, 660 nm, 740 nm, 850 nm, or 940 nm) from one or more light sources (e.g., multiple LEDs) in the tissue of a user. Multichannel signals and/or different light sources may help ensure, for example, that good quality signals may be obtained in a variety of circumstances (e.g., a user moving, walking, running, sleeping, and so forth). In some embodiments, the signal may be obtained from a blood metrics measurement apparatus worn on the wrist of a user.

In step 504, the respiratory rate calculation system pre-processes (e.g., filters) the multichannel signals. In some embodiments, a pre-processing module (e.g., pre-processing module 420) executes pre-processing rules (e.g., rules 448) to filter the multichannel signal.

In step 506, the respiratory rate calculation system determines a spectrum of the multichannel signal. In some embodiments, spectrum rules (e.g., rules 456) are executed by a spectrum module (e.g., module 428) to determine the spectrum of the multichannel signal.

In step 508, the respiratory rate calculation system determines a first respiratory rate from the spectrum of the signal. For example, the first respiratory rate may comprise a noisy respiratory rate which may not accurately reflect an actual respiratory rate. In some embodiments, respiratory rate processing rules (e.g., rules 458) may be executed by a respiratory rate processing module (e.g., module 430) to determine the first respiratory rate.

In step 510, the respiratory rate calculation system obtains a noise reference. For example, the noise reference may be obtained from the estimated spectrum determined in step 506. In some embodiments, the respiratory rate processing module obtains the noise reference.

In step 512, the respiratory rate calculation system obtains one or more second respiratory rates. In some embodiments, one or more second respiratory rates may be previously determined respiratory rates of the user. For example, the one or more second respiratory rates have been obtained within a predetermined amount of time of the current respiratory rate calculation (e.g., the respiratory rates from with 10 seconds of any of the steps 502-512).

In step 514, the respiratory rate calculation system determines a third respiratory rate based on the first respiratory rate, the noise reference, and the one or more second respiratory rates. In some embodiments, the respiratory rate processing module determines the third respiratory rate.

In step 516, the respiratory rate calculation system provides a respiratory rate message regarding the third respiratory rate. In some embodiments, a communication module (e.g., communication module 432) provides the message to the user.

Figure 5B:
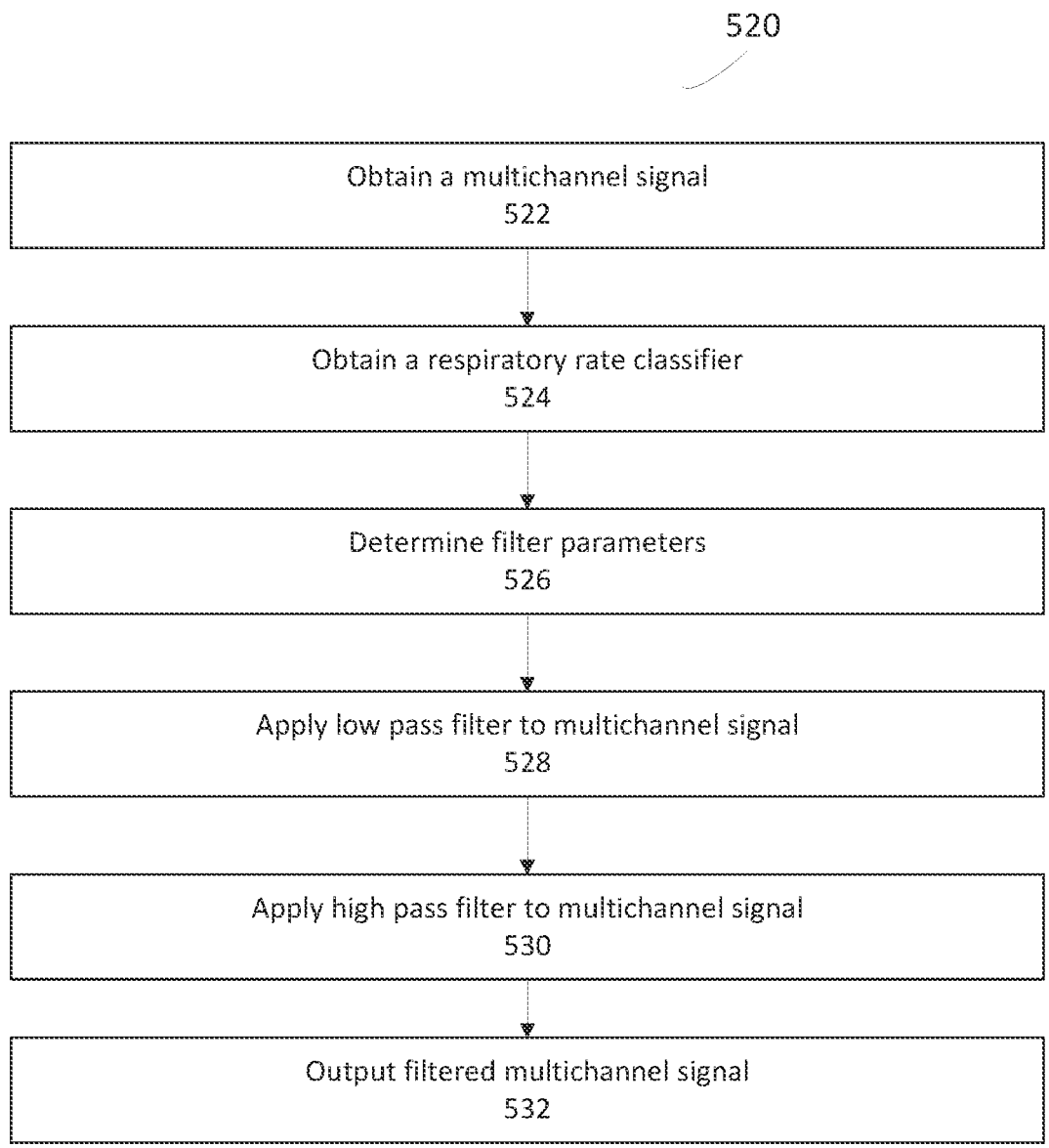
FIG. 5B depicts a flowchart of an example method of operation of a respiratory rate calculation system for filtering multichannel signals according to some embodiments.

FIG. 5B depicts a flowchart 520 of an example method of operation of a respiratory rate calculation system for filtering multichannel signals according to some embodiments.

In step 522, a respiratory rate calculation system obtains a multichannel signal. In some embodiments, the signal may be obtained from a blood metrics measurement apparatus worn on the wrist of a user.

In step 524, the respiratory rate calculation system obtains a respiratory rate classifier. In some embodiments, a classifier module (e.g., module 426) executes classifier rules (e.g., rules 454) to obtain the respiratory rate classifier.

In step 526, the respiratory rate calculation system determines one or more filter parameters. In some embodiments, the classifier module executes the classifier rules to determine the parameters.

In step 528, the respiratory rate calculation system applies a low pass filter to the multichannel signal. In some embodiments, the low pass filter is configured using some or all of the one or more filter parameters. In some embodiments, a pre-processing module (e.g., module 420) configures and/or applies the low pass filter.

In step 530, the respiratory rate calculation system applies a high pass filter to the multichannel signal. In some embodiments, the high pass filter is configured using some or all of the one or more filter parameters. In some embodiments, the pre-processing module configures and/or applies the high pass filter.

In step 532, the respiratory rate calculation system outputs a filtered multichannel signal. In some embodiments, the pre-processing module outputs the filtered multichannel signal.

Figure 6:
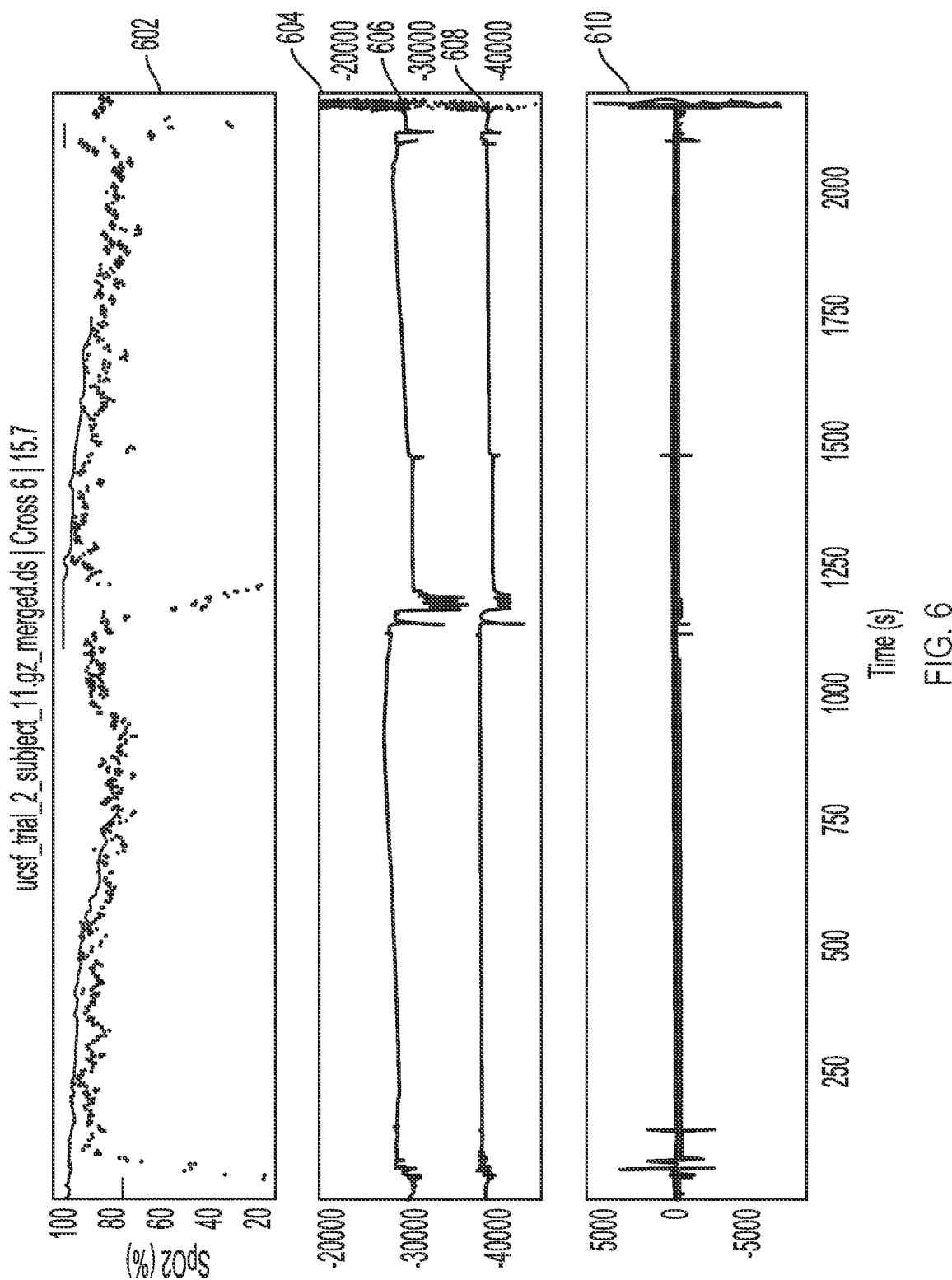
FIG. 6 depicts three plots representing time series associated with a single patient in one example.

FIG. 6 depicts three plots representing time series associated with a single patient in one example. The plots may include data from time series of the patient. The patient may be wearing the blood metrics measurement apparatus 200 which collects measurements (e.g., the data). Plot 602 displays a ground truth (lines) and predicted (dots) values of SpO2 over the duration of data collection. There are significant deviations in our predicted values at times near 100, 1100, and 2200 s.

Plot 604 shows the red (red curve, left axis) and infrared (blue curve, right axis) photodetector signals (PPG) (signals 606 and 608, respectively) collected by the wearable sensor device 100.

The PPG baselines exhibit spikes and large deviations appear near the same times as the deviations in SpO2 predictions. Since the SpO2 values are derived from these two channels of PPG data, it is unsurprising that large-amplitude noise in the PPG may interfere with accurate prediction.

Plot 610 depicts data collected by a 3-axis accelerometer on the wearable sensor device 100, synchronized to the samples of the PPG data. Each trace represents the signal from one axis of the accelerometer (e.g., motion sensor 210), after subtracting the mean value of the recording for that axis. Larger amplitudes of the accelerometer signal indicate changes in acceleration (i.e., motion). While there are clear coincidences of features in the accelerometer data and the PPG data, larger accelerometer features do not necessarily correspond to larger PPG features. In particular, near 1100 s it is easier to identify the motion event from the PPG than the accelerometer.

In various embodiments, the pre-processing module 420 may determine a threshold for signal quality based on one or more signals from the energy receivers and then compare subsequent signals to the thresholds prior to processing. By evaluating one or more qualities of signals (e.g., in comparison to a threshold), substandard, low quality (e.g., noisy) signals may be removed or otherwise filtered out before processing thereby improving accuracy of measurements and improving computational efficiency by using less noisy signals. In various embodiments, the reduction of processing signals that are low quality may also improve battery consumption of a wearable device.

In some embodiments, the pre-processing module 420 may detect time ranges associated with spikes and other changes in the baseline of single-channel PPG or other time-series data. Predictions during these time ranges can then be excluded, such that inaccurate values are not presented to users. The pre-processing module 420 could similarly be applied to accelerometer data or time series from additional sensors for noise rejection or event detection.

In various embodiments, the pre-processing module 420 measures how much variation there is in a short window of signal around the time of interest and compares that to a known reference for how much variation is expected. In one example, the threshold for acceptable variation is obtained empirically by considering windows of signal at times when measuring SpO2 is accurate.

The amount of change in a signal in a given window of time can be expressed using a variety of metrics. In one example, the pre-processing module 420 may use the difference between the largest and smallest values in a time window such as the difference between the 5th and 95th percentiles of values in the window or the standard deviation of the values in the window.

To determine the validity of signal at a time t, the wearable may extract a signal window, s, of duration w, centered at time t. The pre-processing module 420 may compute the normalized standard deviation of the window:

$$\sigma_s = \frac{\sqrt{\frac{1}{N}\sum_i (x_i - x)^2}}{x}$$

Where:

$$x = \frac{1}{N}\sum_i x_i$$

In the equations above, xi represent the individual samples included in s. The normalization by the mean of the signal window may be significant for the PPG application, as different levels of brightness of the source LEDs result in a linear scaling of the PPG signal. By normalizing, the amount of variation is computed per unit brightness.

A threshold, $\sigma_{max}$, may specify that the signal at t is invalid if $\sigma_s > \sigma_{max}$.

In one example, to determine the value of $\sigma_{max}$, the blood metrics measurement apparatus 200 may collect SpO2 measurements (e.g., predictions) from a training set of PPG recordings. SpO2 may be estimated according to the following:

$$SpO_2 = 115 - 25\left(\frac{r_R}{r_{IR}}\right)$$

where $r_R$ is the wavelength of the red LED and $r_{IR}$ is the wavelength of the infrared LED.

$$r_\lambda = \frac{p_{90,\lambda} - p_{10,\lambda}}{s_\lambda}$$

The equation above is the difference between the 90th and 10th percentiles of the red (R) or infrared (IR) PPG signals, normalized by the mean of the signal window. The windows sR and sIR may be selected with the same width w to be used for signal validity, and may be associated with the time at the center of the windows. Predictions at each time may be compared against corresponding ground truth SpO2 values—all windows, both red and infrared, associated with times where the predicted SpO2 value are within 1% absolute of ground truth may be added to a set 102. The normalized standard deviation, as defined above, may be computed for all windows in χ, and $\sigma_{max}$ may be taken as the 99th percentile of the resulting values.

Figure 7:
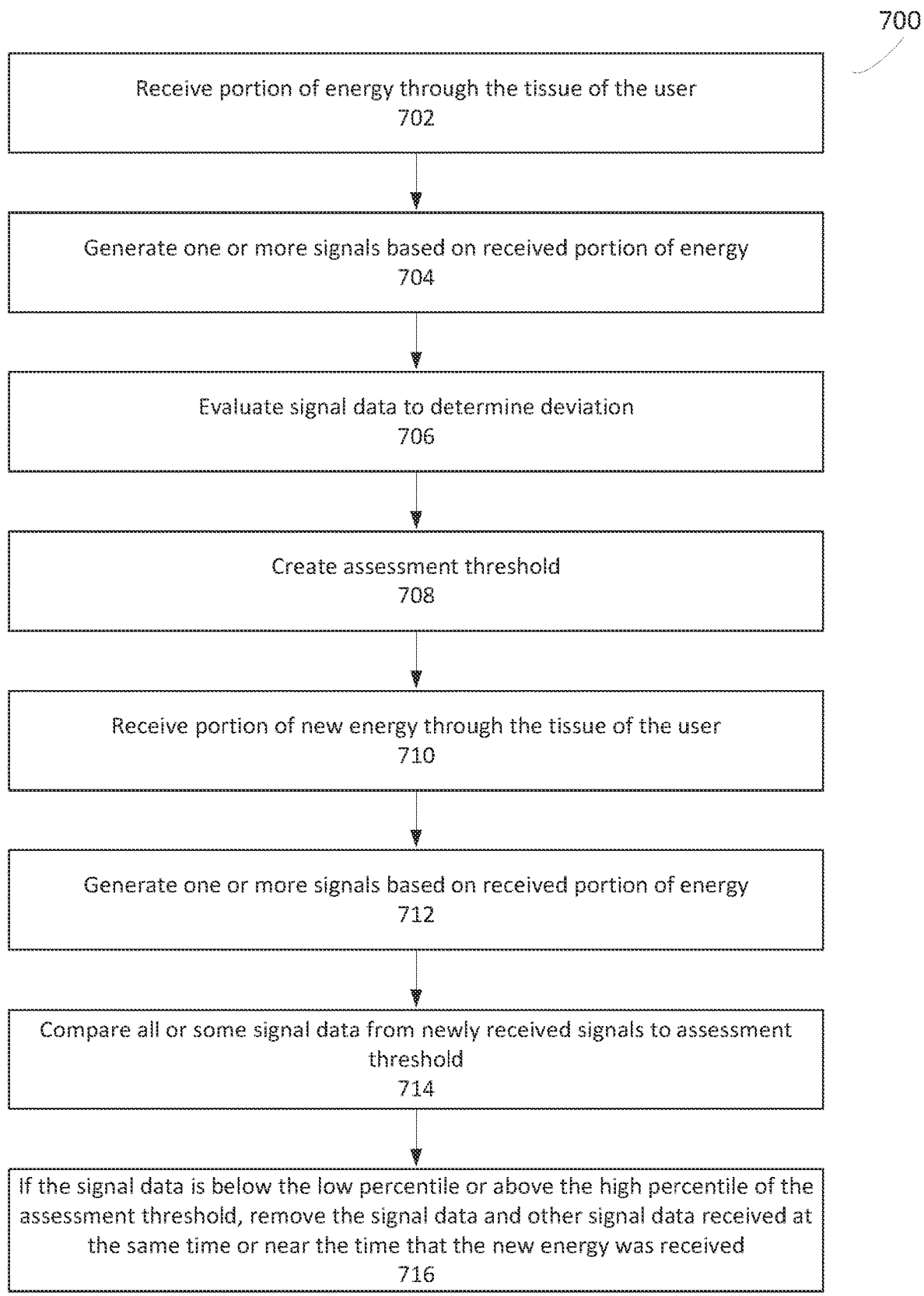
FIG. 7 is a flowchart for assessing signals from a blood metrics measurement apparatus (e.g., a wearable sensor device) that measures SpO2 of the wearer in some embodiments.

FIG. 7 is a flowchart 700 for assessing signals from a blood metrics measurement apparatus (e.g., a wearable sensor device) that measures SpO2 of the wearer in some embodiments. As discussed herein, the blood metrics measurement apparatus 200 may generate signals based on measurements taken of a patient. A set of signals may be assessed to determine if the signals are of sufficient quality (e.g., lacking in noise) before assessing the signals and similar signals taken at or near the time of assessment. By eliminating noisy signals, the accuracy of prediction may be improved, computation efficiency (e.g., speed and scale) may be improved, and battery power extended (e.g., by not processing the data from the poor quality, noisy, signals and other signals that may be generated at or near the time of the poor quality, noisy, signals).

Although this flowchart discusses establishing thresholds and assessing signals to measure SpO2, it will be appreciated that the same methods may be applied to many different measurements including, for example, respiratory rate, blood pressure, heart rate, and/or the like.

In various embodiments, the blood metrics measurement apparatus 200 may determine an assessment threshold to compare signals based on previously received signals of the blood metrics measurement apparatus 200. The signals used to create the assessment threshold may be of the same quality (e.g., wavelength) as those signals which are compared against the assessment threshold. In some embodiments, the blood metrics measurement apparatus 200 may create the assessment threshold based on signals received from a wearer of the blood metrics measurement apparatus 200 and then use the assessment threshold to evaluate or validate subsequently received signals from the same wearer. In other embodiments, the assessment threshold may be calibrated or may be based on data of other users or based on expected results (e.g., the assessment threshold may be stored within the blood metrics measurement apparatus 200 prior to the wearer wearing the blood metrics measurement apparatus 200).

In step 702, the blood metrics measurement apparatus 200 may receive a portion of energy through the tissue of the wearer. A transmitter of the blood metrics measurement apparatus 200 may project energy into the tissue of the wearer and a sensor or receiver may receive a portion of the transmitted energy reflected back from the tissue of the user. The energy may be of a wavelength for measuring a physiological characteristic such as respiratory rate, SpO2, blood pressure, heart rate, or the like.

In step 704, the blood metrics measurement apparatus 200 generates signals based on the portion of energy. The signals may include time series data (e.g., windows of time series data). The windows of time series data may then be used for evaluation of a variation of the data to establish a known reference. In various embodiments, any number of windows extending over any amount of time may be used to create the evaluation.

In some embodiments, periodically, the evaluation (e.g., assessment threshold) may be compared against variability of newly received signals to periodically reevaluated the threshold. If the variation of the data is sufficiently different than the previously created assessment threshold (e.g., there is a significantly different standard deviation such as more than a 3% shift), then the assessment threshold may be re-created using all or some new data of new or more recent time windows.

In step 706, all or some of the time series data of the windows may be evaluated to determine a deviation within the data of the signals. For example, the pre-processing module 420 measures how much variation there is in a short window of signal around the time of interest and compares that to a known reference for how much variation is expected. In one example, the threshold for acceptable variation is obtained empirically by considering windows of signal at times when measuring SpO2 is accurate.

The amount of change in a signal in a given window of time can be expressed using a variety of metrics. In one example, the pre-processing module 420 may use the difference between the largest and smallest values in a time window such as the difference between the 10th (low) and 90th percentiles (high) of values in the window or the standard deviation of the values in the window:

$$\sigma_s = \frac{\sqrt{\frac{1}{N}\sum_i (x_i - x)^2}}{x}$$

Where:

$$x = \frac{1}{N}\sum_i x_i$$

as discussed herein.

As also discussed herein, a threshold, $\sigma_{max}$, may specify that the signal at t is invalid if $\sigma_s > \sigma_{max}$. In one example, to determine the value of $\sigma_{max}$, the blood metrics measurement apparatus 200 may collect SpO2 measurements (e.g., predictions) from a training set of PPG recordings. SpO2 may be estimated according to the following:

$$SpO_2 = 115 - 25\left(\frac{r_R}{r_{IR}}\right)$$

where $r_R$ is the wavelength of the red LED and $r_{IR}$ is the wavelength of the infrared LED.

$$r_\lambda = \frac{p_{90,\lambda} - p_{10,\lambda}}{s_\lambda}$$

The equation above is the difference between the 90th and 10th percentiles of the red (R) or infrared (IR) PPG signals, normalized by the mean of the signal window. The windows sR and sIR may be selected with the same width w to be used for signal validity, and may be associated with the time at the center of the windows. Predictions at each time may be compared against corresponding ground truth SpO2 values—all windows, both red and infrared, associated with times where the predicted SpO2 value are within 1% absolute of ground truth may be added to a set $\chi$. The normalized standard deviation, as defined above, may be computed for all windows in $\chi$.

It will be appreciated that any percentiles may be utilized for the assessment threshold.

In step 708, the assessment threshold is created based on the variation. In various embodiments, the assessment threshold includes the range of low percentile values and/or the range of high percentile values (e.g., 10% and 90%, or 5% and 95%, or the like). All or some of the subsequently receive signals of similar energy (e.g., similar or same wavelength) may be evaluated against the assessment threshold to determine if the signals are within the extreme of the variation (either upper or lower). If so, the signals may be removed or filtered so that further processing is not performed on those signals.

It may be appreciated that periodic samples of signal may be evaluated against the assessment threshold (e.g., every few minutes, seconds, hours, or the like). In some embodiments, samples of signals are constantly evaluated against the assessment threshold.

In step 710, the blood metrics measurement apparatus 200 may receive another portion of energy through the tissue of the wearer.

In step 712, the blood metrics measurement apparatus 200 generates signals based on the portion of energy.

In step 714, all or some time windows of the signals may be compared against the assessment threshold to determine if the signal data of the newly generated signals are below a low percentile of variability (e.g., 10% or below) or above a high percentile of variability (e.g., 90% or above).

In step 716, if the signal data of the newly generated signals is below the low percentile of variability or above the high percentile of variability, the energy and/or signals associated with the newly acquired data (e.g., signals associated with the windows of the newly received data and/or signals generated at or near the time the signal data was assessment) may be removed from further processing.

The remaining data or future data that passes the assessment threshold (e.g., above the low percentile and below the high percentile) may be assessed as discussed herein to create estimates and/or measurements.

Figure 8:
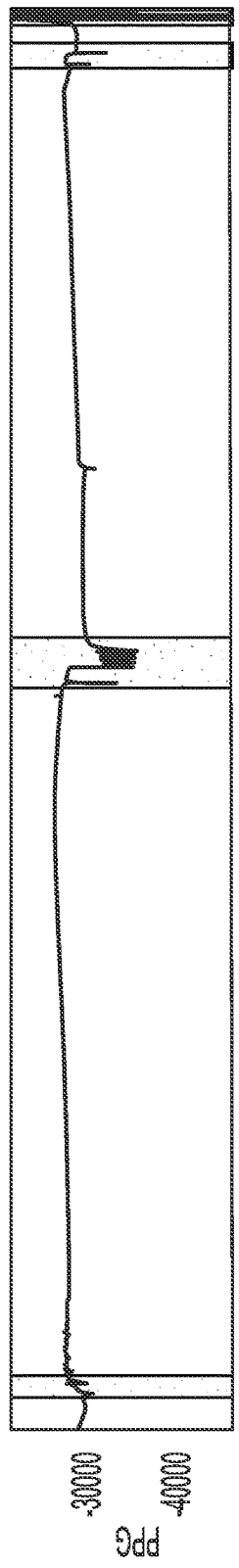
FIG. 8 depicts an application of the artifact removal algorithm to red PPG data and original PPG data.
Figure 8:
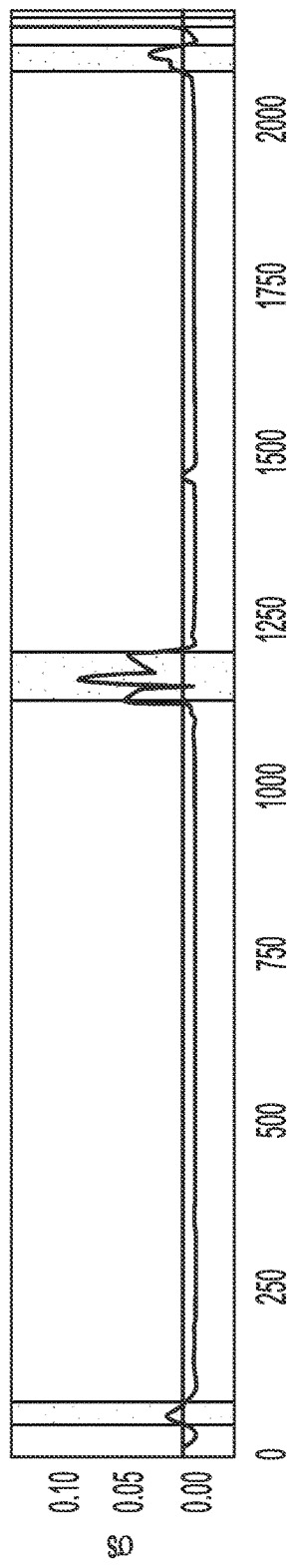

FIG. 8 depicts an application of the artifact removal algorithm to red PPG data and original PPG data. σs computed at all times corresponding to PPG samples, in the lower plot and the line indicates $\sigma_{max}$. Shaded regions indicate times when σs exceeds $\sigma_{max}$. These regions can thus be excluded from further data processing.

Figure 9:
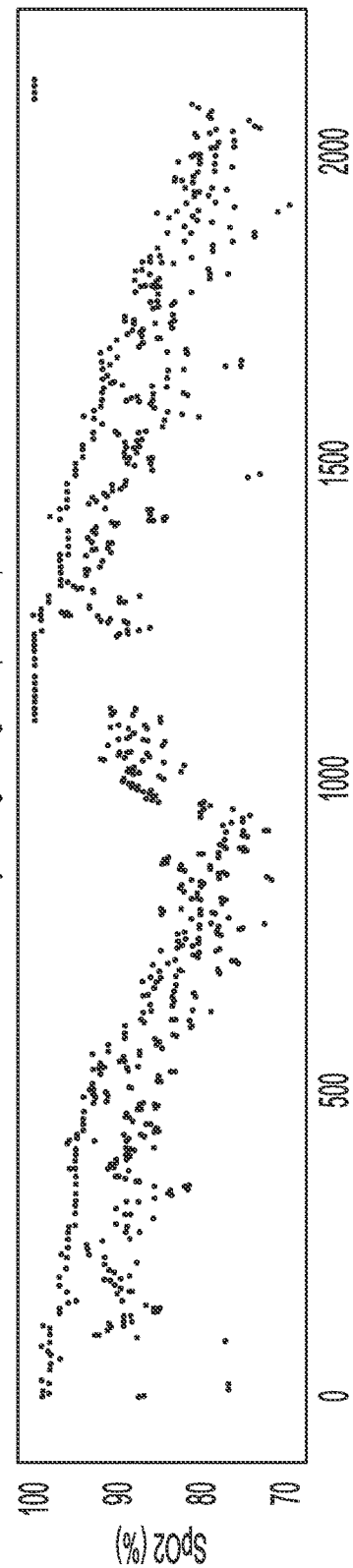
FIG. 9 depicts the segments of data classified as artifacts that may be rejected using a window duration of w=20 s.

FIG. 9 depicts the segments of data classified as artifacts that may be rejected using a window duration of w=20 s. The pre-processing module 420, in this example, has successfully identified features. Several small artifacts remain depending on the application and sensitivity to noise, the threshold and window duration can be adjusted to precisely control how aggressively to reject such artifacts.

In various embodiments, the pre-processing module 420 may include tip functionality. The tip functionality may include utilizing signals received by at least one receiver of the blood metrics measurement apparatus 200 to assess whether other signals received by other receivers of the blood metrics measurement apparatus 200 are likely to be of sufficient quality before performing assessments on the other signals. In one example, a signal taken at the top of the wearer's wrist (near the back of the hand) may be utilized to determine whether a signal taken at the bottom of the wearer's wrist (near the palm of the hand) may be processed and used for measurements.

As discussed herein, non-invasive medical devices and physiological sensors commonly monitor vital signs using photoplethysmograph (PPG) signals. PPG signals, however, are sensitive to various parameters, such as degree of motion, measurement site on the body, penetration depth (as defined by vasculature and tissue interface with the specific optical wavelength), skin color, sweat, dirt and more. Controlling these parameters is often quite difficult, or impossible. Nonetheless, the ability to obtain useable PPG signal is key to monitoring vital signs with medical-grade accuracy.

Due to the challenge described above, there is a strong need for a way to identify a clear and high signal-to-noise reference signal for the PPG waveform. PPG waveforms may be extracted by the blood metrics measurement apparatus 200 from multiple sites around the wearer's wrist in order to measure vital signs and overcome noise issues.

Often there are applications that require sampling of PPG signals from locations with low PPG signal quality, such as the bottom of the wrist, or locations with lower perfusion. Locations which are highly perfused and have significant capillary tissue present, such as the finger, eye blood vessels or the top of the wrist, have much better signal. However, those sites do not always contain information about a desired vital sign or biomarker. For instance, PPG signals may readily be measured with wavelengths in the green range of the visible spectrum (~550 nm) in superficial capillary beds on the back of the wrist.

PPG signal measured in the red or infrared ranges of the spectrum (660, 940 nm) is more useful for monitoring blood oxygen saturation (SpO2), but due to longer penetration distances these wavelengths are more susceptible to noise from anatomical effects deeper in the tissue. For monitoring blood pressure, it is preferable to isolate the PPG signal arising in the deep arteries, which the relatively short penetration of green light is unable to access. Furthermore, accessing the radial artery may require introduction of undesired signal contributions from the deep veins in the wrist.

By eliminating noisy signals, the accuracy of prediction may be improved, computation efficiency (e.g., speed and scale) may be improved, and battery power extended (e.g., by not processing the data from the poor quality, noisy, signals and other signals that may be generated at or near the time of the poor quality, noisy, signals).

Figure 10A:
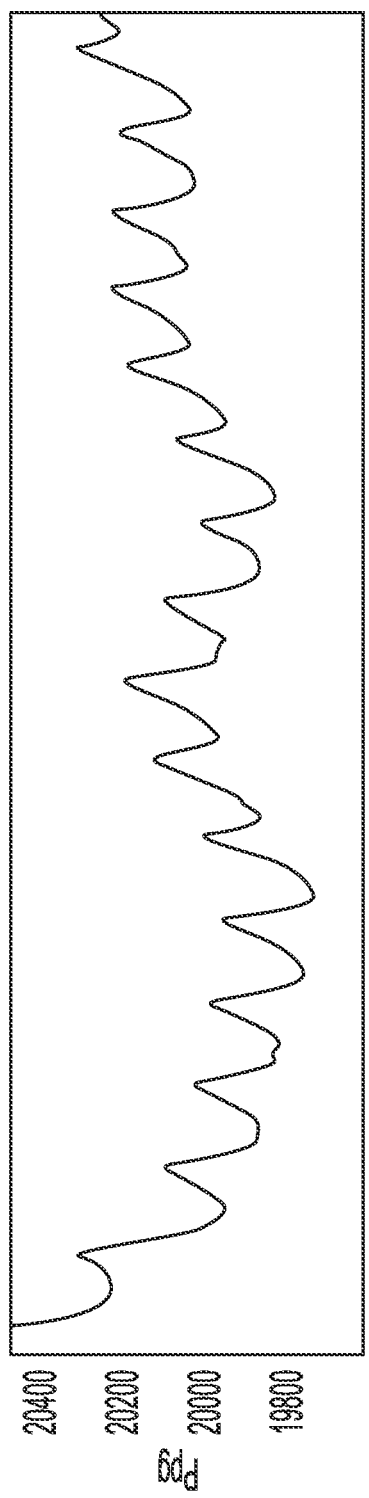
FIG. 10a is an example of a high SNR signal.
Figure 10B:
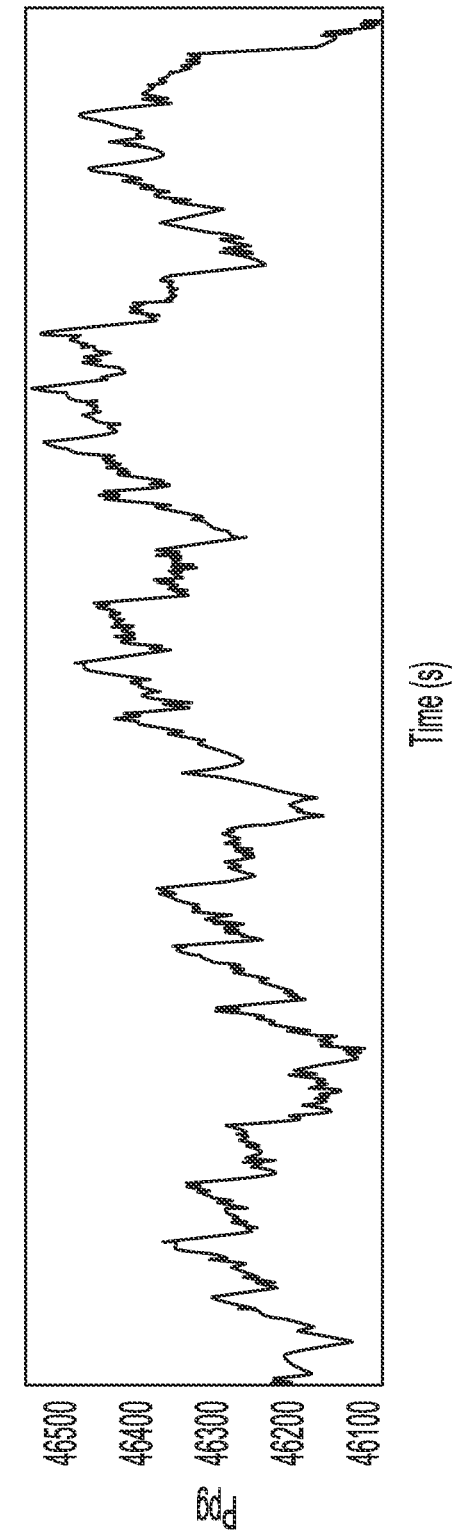
FIG. 10b is an example of a low SNR signal.

In various embodiments, the pre-processing module 420 may use PPG signals from a specific site with a specific wavelength as a reference to another PPG sensor on low signal quality or low perfusion location. The reference signal is applied to an adaptive system such as a filter that allows for the extraction of a PPG signal from the low signal quality location with a significantly higher signal-to-noise ratio (SNR). FIG. 10*a* is an example of a high SNR signal. FIG. 10*b* is an example of a low SNR signal.

It may be appreciated that the blood metrics measurement apparatus 200 may include any number of PPG sensor arrays. At least one array may be at the top of the wearer's wrist. In one example, one array may include LED emitters at three wavelengths and a single photodiode. This array may provide high SNR PPG reference signals, especially in the green wavelength, due to low penetration depth in that wavelength and the existence of superficial capillary tissue at the measurement site. A second array may contain eight three-wavelength LED emitters and eight photodiodes. SNR varies greatly across the different possible LED-photodiode (emitter-receiver) pairs.

For specific vital signs such as blood pressure, respiratory rate and arterial SpO2, the physiological information necessary for inferring vital signs is contained specifically in the PPG signal associated with the arteries. Sampling multiple locations on the bottom of the wrist allows for the acquisition of a mixed signal—with arterial, venous, capillary and other sources mixed in. Using the reference signal described above, it is possible to extract key features that are unique to capillary and arterial signals and allow for the separation of signals due to arterial and capillary blood pulsation from signals due to venous blood. These features contain wave features described in previous art such as kurtosis, frequency, rise rate, a/b ratios, spectral features and wavelet features.

The output of this source separation procedure may be PPG signal from an arterial-capillary source. The processing is computationally resource intensive and beyond the capabilities of most MPUs. Furthermore, the amount of memory required for the processor to make a measurement is usually beyond the capacity of the ordinary MPU. As a result, the procedure take time, processing power, and energy. If the PPG signals from an arterial-capillary source have too much noise (low SNR), then the result will be a waste of time, processing power, and energy (and/or simply inaccurate). The procedure discussed as follows enables PPG signals from the arterial-capillary source to be taken when the result is likely to be higher in SNR or captured PPG signals to be rejected if the result is likely to have low SNR.

The problem is reducing the resource burden of a data collection system at low signal quality locations (e.g., at the wrist near the palm) by using a tip-off mechanism located at high signal quality locations (e.g., at the top of the wrist near the back of the hand).

Figure 11:
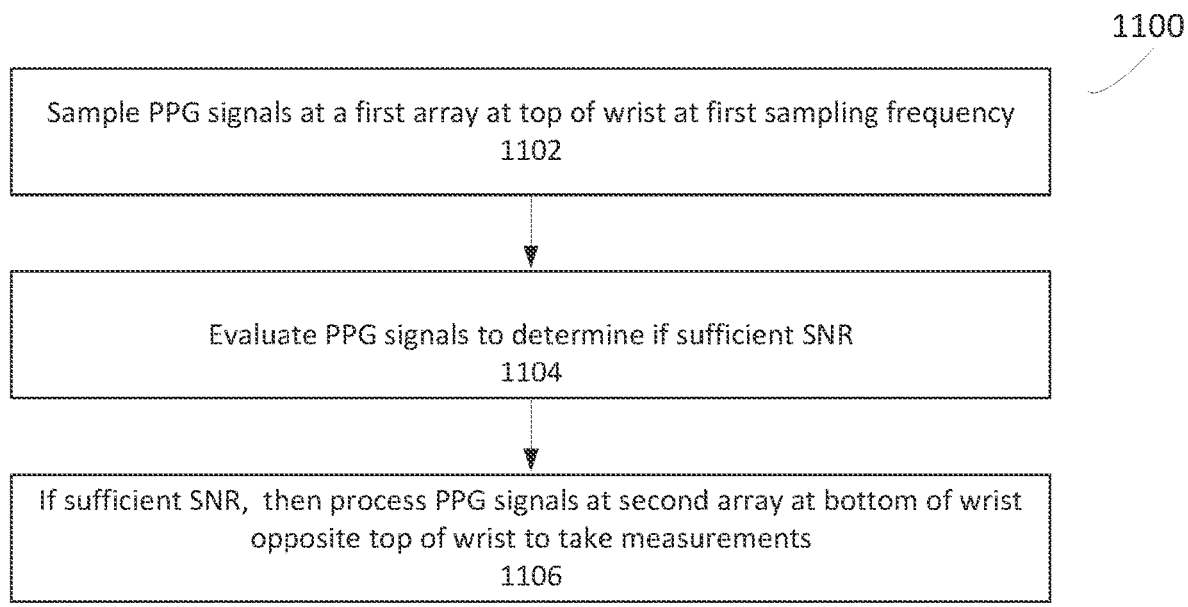
FIG. 11 is a flowchart for reducing a burden of a high-bandwidth blood quality (e.g., SpO2, respiratory rate, or blood pressure) computation to a low-bandwidth computation of tip-offs.

FIG. 11 is a flowchart 1100 for reducing a burden of a high-bandwidth blood quality (e.g., SpO2, respiratory rate, or blood pressure) computation to a low-bandwidth computation of tip-offs. Tip-offs are moments in which the blood pressure collection system is signaled to record data due to a metric of signal quality calculated at a spatially relevant location.

In step 1102, the blood metrics measurement apparatus 200 uses a first array to sample PPG signals at spatially relevant locations with high SNR PPG signals to be used as a tip-off mechanism for a blood data collection system. In the case of the wrist, the transmitter/receiver pairs at the top of the wrist are less resource intensive (from a memory/power standpoint) than the sensor array at the bottom of the wrist designed for blood data collection.

Due to the computational efficiency of processing, blood pressure measurements at the top of the wrist may be made a greater sampling frequency (e.g., a first sampling frequency) than processing measurements at the bottom of the wrist (e.g., positions with a lower SNR). Further sampling signals at the top of the wrist may be made with a larger number of, or significantly different set of transmitter/receiver pairs as compared to the bottom of the wrist. As a result, the tip-off mechanism above the wrist can be used for pinpointing opportune moments in which data collected at the bottom of the wrist is likely to contain valid blood pressure information.

In step 1104, the blood metrics measurement apparatus 200 compares any number of sampled PPG signals to a threshold to determine if the signals have sufficient an SNR. In other embodiments, SNR may be estimated in the sampled PPG signals to determine if the estimated SNR is above a quality threshold. If the sampled PPG signals have sufficient SNR and/or are above the quality threshold, then signals may be taken at a second array of the blood metrics measurement apparatus 200. In this example, the second array of the blood metrics measurement apparatus 200 is located in a different position from the first array.

In some embodiments, the energy is not transmitted into the wearer at the second array until the sampled PPG signals from the first array are of sufficient quality. In this example, battery power may be further preserved by not triggering the LEDs of the second array until there is sufficient likelihood of being able to capture quality information. In various embodiments, signals are not created from energy reflected from the wearer using the second array until the sampled PPG signals from the first array are of sufficient quality. In further embodiments, signals are created based on energy reflected from the wearer using the second array but the signals are not processed until the sampled PPG signals from the first array are of sufficient quality.

In various embodiments, the sampled PPG signals at the first array may be used to create an assessment threshold in a manner discussed regarding FIG. 7. Subsequent sampled PPG signals at the first array may then be compared against the assessment threshold to determine if the PPG signals are not in the extremes of the determined deviations. If the PPG signals are in either extreme, then signals at the second array may not be processed, created, or received. If the PPG signals are not in either extreme, then the signals at the second array may be received, created, and/or processed.

In step 1106, if the sampled PPG signals from the first array have sufficient SNR, then the blood metrics measurement apparatus 200 may process PPG signals from the second array.

In some examples, the computational and power requirements are reduced by limiting the higher frequency of tip-off computations to low bandwidth data collected from the top of the wrist. The memory requirements may be reduced because the high bandwidth data collected for blood pressure, respiration rate, SpO2, or heart rate may only needs to be stored when signaled by the tip-off mechanism. The sensor array at the bottom of the wrist can be enabled/disabled based on information from the top of the wrist. This tip-off mechanism reduces the need to collect blood pressure data indefinitely.

The blood metrics measurement apparatus 200 may have a validity mechanism to prevent the visual nuisance of visible LEDs during human wrist detection. In various embodiments, the blood metrics measurement apparatus 200 may perform human wrist detection using predetermined infrared signals and a dual set of receivers while limiting the impact of physiological mistriggers during human wrist detection.

A common problem in wearables is detecting if a human is wearing a device. This detection mechanism may prevent unnecessary resource consumption of the device (preserving memory usage and battery power) as well as temporally bounding the device's data collection/measurement windows to moments in which a human (i.e., a wearer) is present.

When a wearable detects human presence, it is common for wearables to use light emitted from LEDs to make non-invasive determinations of physiological measurements. This light can be a visual nuisance. This process eliminates the visual nuisance during human presence detection by using infrared light.

Human presence detection can be achieved using sensors spatially located on a wearable to create an infrared trip mechanism. The infrared trip reduces the need of performing a validity check within the visible spectrum (eliminating the visual nuisance) since the human eye is not sensitive to infrared wavelengths.

Figure 12:
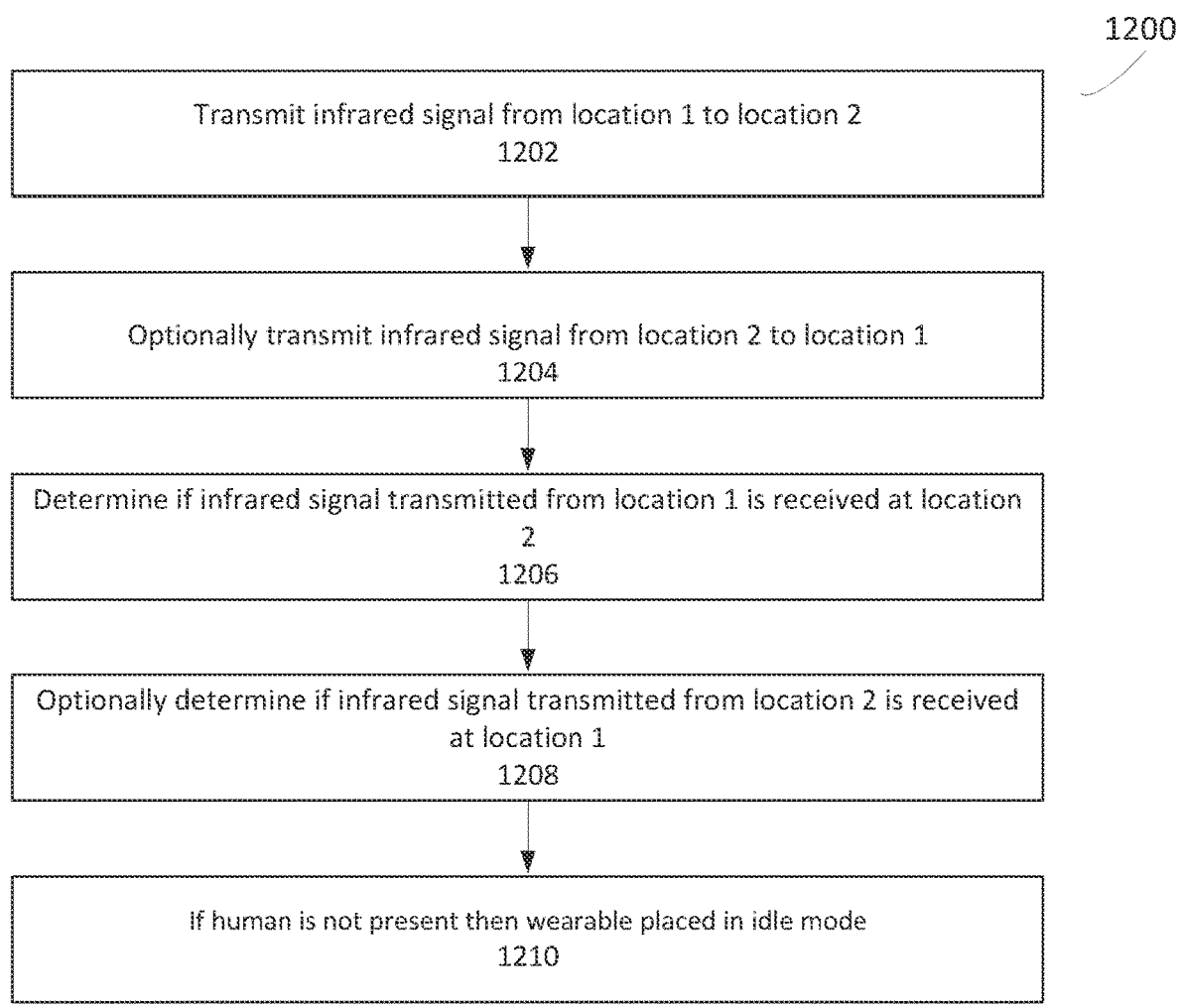
FIG. 12 is a flowchart to perform human presence detection for a blood metrics measurement apparatus.

FIG. 12 is a flowchart 1200 to perform human presence detection for a blood metrics measurement apparatus 200. The process may reduce a burden of a high-bandwidth blood quality (e.g., SpO2, respiratory rate, heart rate, or blood pressure) computation to a low-bandwidth computation of tip-offs. Tip-offs are moments in which the blood pressure collection system is signaled to record data due to a metric of signal quality calculated at a spatially relevant location.

Figure 13:
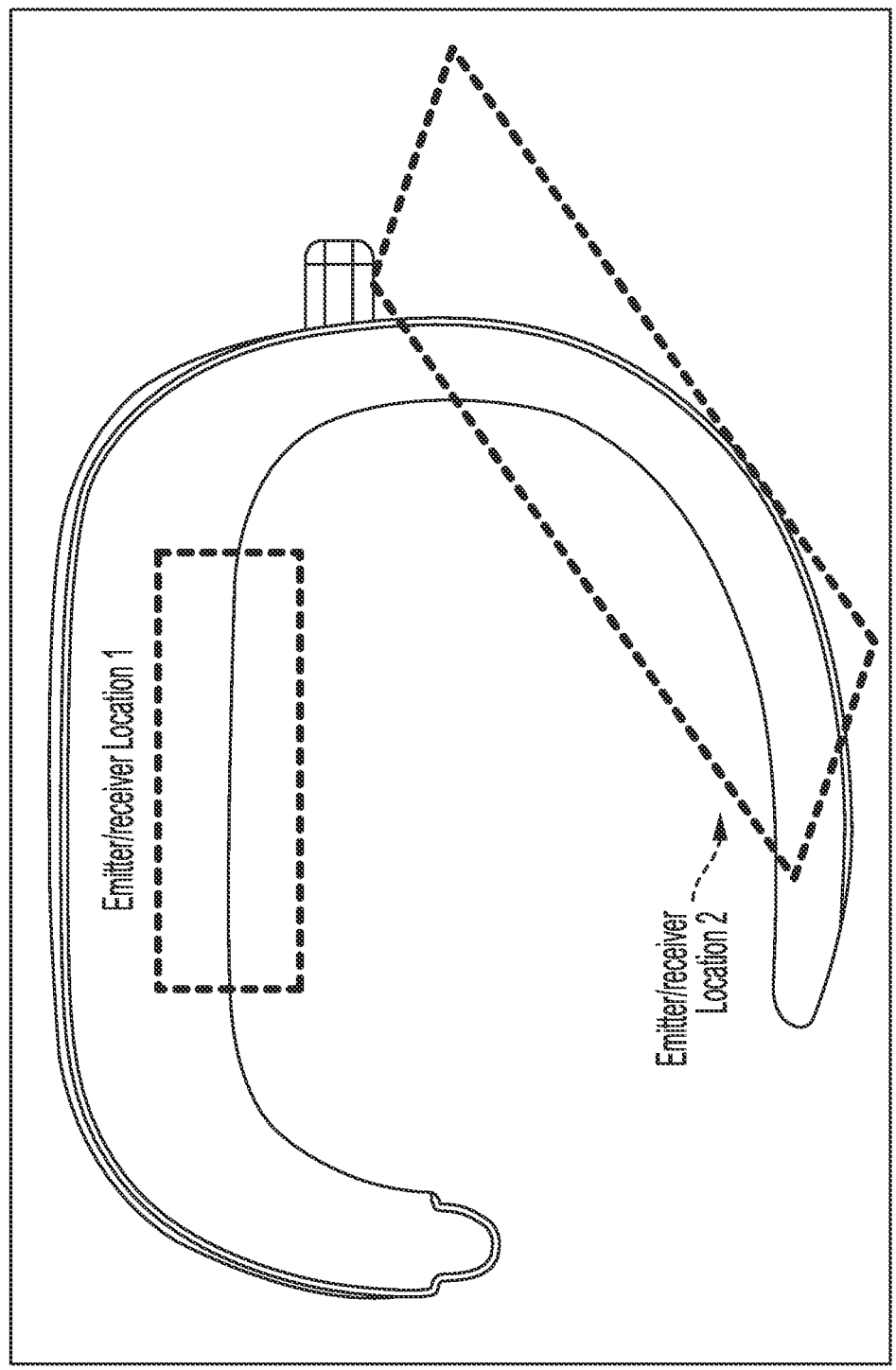
FIG. 13 depicts a blood metrics measurement apparatus such as wearable sensor device in some embodiments.

In step 1202, the blood metrics measurement apparatus 200 may perform human presence detection by transmitting a known infrared signal from location 1 to location 2. FIG. 13 depicts a blood metrics measurement apparatus 200 such as wearable sensor device 100. The blood metrics measurement apparatus 200 may transmit the known infrared signal at a first transmitter and/or array to a second transmitter and/or array. The first location may be opposite the second location such that the path of the infrared signal crosses an opening defined by the blood metrics measurement apparatus 200 for wrapping around a wrist or other body part of the wearer.

In optional step 1204, the blood metrics measurement apparatus 200 may transmit a known infrared signal from location 2 to location 1.

In step 1206, the blood metrics measurement apparatus 200 determines if the infrared signal transmitted from location 1 is received by location 2. Similarly, in optional step 1208, the blood metrics measurement apparatus 200 determines if the infrared signal transmitted from location 2 is received by location 1

Figure 14A:
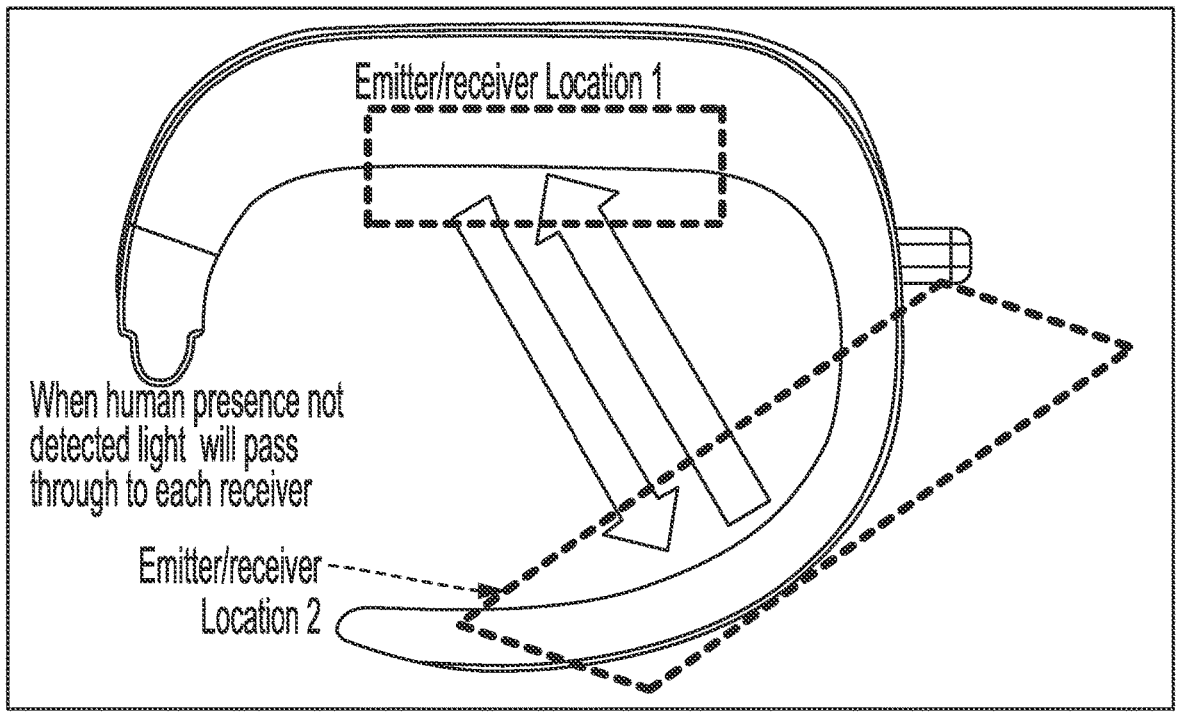
FIG. 14a depicts the signals being received by the first and second locations to determine that a wearer is not present in some embodiments.

If the signal is received at location two and/or location 1, the blood metrics measurement apparatus 200 may conclude that a human is not present. FIG. 14*a* depicts the signals being received by the first and second locations to determine that a wearer is not present. If a human is not present then wearable shall be placed in idle mode and the device shall not perform physiological measurements in step 1210.

Figure 14B:
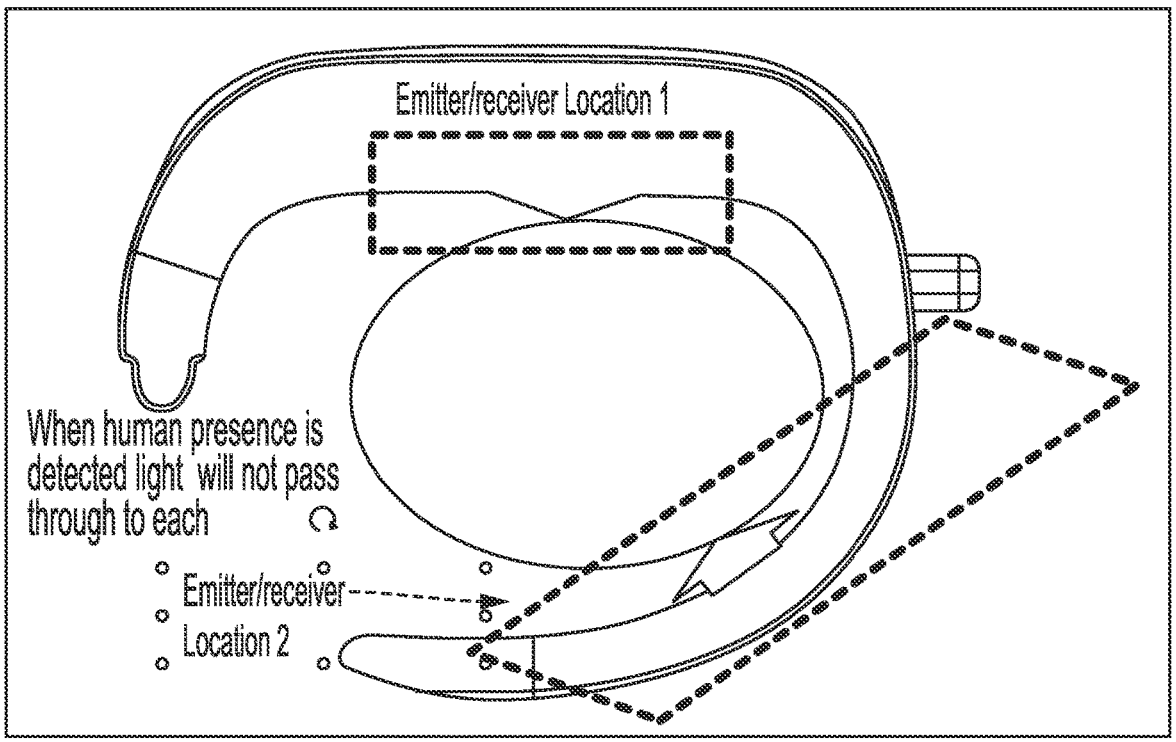
FIG. 14b depicts the signals not being received by the first and second location because the signals are blocked by the wearer's body in some embodiments.

To perform the human presence detection a known infrared signal is transmitted from location 1 to location 2 and/or a known infrared signal is transmitted from location 2 to location 1. FIG. 14*b* depicts the signals not being received by the first and second location because the signals are blocked by the wearer's body. If the signal is not received at location two and/or location 1, the blood metrics measurement apparatus 200 determines that a human has been detected. If a human has been detected, the blood metrics measurement apparatus 200 may function normally and perform physiological measurements.

It will be appreciated that a "user device," "apparatus," "server," "module," "system," and/or "database" may comprise software, hardware, firmware, and/or circuitry. In one example, one or more software programs comprising instructions capable of being executable by a processor may perform one or more of the functions of the user devices, servers, modules, systems, and/or databases described herein. In another example, circuitry may perform the same or similar functions. Alternative embodiments may comprise more, less, or functionally equivalent user devices, apparatus, servers, modules, systems, and/or databases, and still be within the scope of present embodiments.

The present invention(s) are described above with reference to example embodiments. It will be appreciated that various modifications may be made and other embodiments may be used without departing from the broader scope of the present invention(s). Therefore, these and other variations upon the example embodiments are intended to be covered by the present invention(s).

What is claimed is:

1. A wearable medical device for monitoring at least one physiological parameter of a patient with improved accuracy by removing noisy signals, comprising:
an energy transmitter disposed in the wearable medical device configured to project energy toward tissue of a patient;
an energy receiver disposed in the wearable medical device configured to detect energy received from the tissue of the patient and generate at least one signal based on the detected energy, the at least one signal comprising time series data;
a processor and associated memory, the memory configured to store executable instructions that are executed by the processor, the instructions being executable to:
receive a first signal from the energy receiver,
identify a first at least one window of the first signal including first time series data,
evaluate a variation among the first time series data in the first at least one window,
create an assessment threshold based on the variation of the first time series data in the first at least one window,
receive a second signal from the energy receiver,
identify a second at least one window of the second signal including second time series data,
compare the second time series data against the assessment threshold, and
remove the second signal from further processing if the second time series data does not pass the assessment threshold.

2. The wearable medical device of claim 1, wherein the first at least one window includes separate windows for validating red and infrared PPG signals, respectively.

3. The wearable medical device of claim 1, wherein the assessment threshold comprises at least one of a predetermined low percentile of variability and a predetermined high percentile of variability such that if the second time series data is below the low percentile of variability or above the high percentile of variability, the second signal is removed from further processing.

4. The wearable medical device of claim 3, wherein the predetermined low and high percentiles of variability are determined by calculating a standard deviation of values in the second at least one window.

5. The wearable medical device of claim 1, wherein the assessment threshold is re-created based on an evaluation of a variation of the second time series data.

6. The wearable medical device of claim 5, wherein the assessment threshold is re-created periodically.

7. The wearable medical device of claim 5, wherein the assessment threshold is re-created if a change of standard deviation of the second time series data exceeds a predetermined amount.

8. The wearable medical device of claim 1, wherein the first and second signals comprise red and infrared PPG signals.

9. The wearable medical device of claim 1, wherein the wearable medical device is a wrist-worn device.

10. A method for monitoring at least one physiological parameter of a patient with improved accuracy by removing noisy signals based on signals detected by a wearable medical device, the method comprising:
projecting energy toward tissue of a patient with an energy transmitter disposed in the wearable medical device;
detecting energy received from the tissue of the patient and generating at least one signal based on the detected energy with an energy receiver disposed in the wearable medical device, the at least one signal comprising time series data;
receiving a first signal from the energy receiver by a processor disposed in the wearable medical device;
identifying a first at least one window of the first signal including first time series data;
evaluating a variation among the first time series data in the first at least one window;
creating an assessment threshold based on the variation of the first time series data in the first at least one window;
receiving a second signal from the energy receiver by the processor;
identifying a second at least one window of the second signal including second time series data;
comparing the second time series data against the assessment threshold; and
removing the second signal from further processing if the second time series data does not pass the assessment threshold.

11. The method of claim 10, wherein the first at least one window includes separate windows for validating red and infrared PPG signals, respectively.

12. The method of claim 10, wherein the assessment threshold comprises at least one of a predetermined low percentile of variability and a predetermined high percentile of variability such that if the second time series data is below the low percentile of variability or above the high percentile of variability, the second signal is removed from further processing.

13. The method of claim 12, wherein the predetermined low and high percentiles of variability are determined by calculating a standard deviation of values in the second at least one window.

14. The method of claim 10, wherein the assessment threshold is re-created based on an evaluation of a variation of the second time series data.

15. The method of claim 14, wherein the assessment threshold is re-created periodically.

16. The method of claim 14, wherein the assessment threshold is re-created if a change of standard deviation of the second time series data exceeds a predetermined amount.

17. A computer program product for operating a wearable medical device comprising at least one non-transitory computer-readable medium including one or more instructions that, when executed by at least one processor, cause the at least one processor to:
  receive a first signal detected by an energy receiver of the wearable medical device, wherein the first signal is based on energy projected toward tissue of a patient and received from the tissue of the patient by the energy receiver;
  identify a first at least one window of the first signal including first time series data;
  evaluate a variation among the first time series data in the first at least one window;
  create an assessment threshold based on the variation of the first time series data in the first at least one window;
  receive a second signal from the energy receiver, wherein the second signal is based on energy projected toward the tissue of the patient and received from the tissue of the patient by the energy receiver;
  identify a second at least one window of the second signal including second time series data;
  compare the second time series data against the assessment threshold; and
  remove the second signal from further processing if the second time series data does not pass the assessment threshold.

18. The computer program product of claim 17, wherein the first at least one window includes separate windows for validating red and infrared PPG signals, respectively.

19. The computer program product of claim 17, wherein the assessment threshold comprises at least one of a predetermined low percentile of variability and a predetermined high percentile of variability such that if the second time series data is below the low percentile of variability or above the high percentile of variability, the second signal is removed from further processing.

20. The computer program product of claim 19, wherein the predetermined low and high percentiles of variability are determined by calculating a standard deviation of values in the second at least one window.

21. The computer program product of claim 17, wherein the assessment threshold is re-created based on an evaluation of a variation of the second time series data.

22. The computer program product of claim 21, wherein the assessment threshold is re-created periodically.

23. The computer program product of claim 21, wherein the assessment threshold is re-created if a change of standard deviation of the second time series data exceeds a predetermined amount.

* * * * *